United States Patent
Burq et al.

(10) Patent No.: US 12,334,189 B2
(45) Date of Patent: Jun. 17, 2025

(54) SYSTEM AND METHOD FOR PROCESSING EXPERIMENTAL DATA

(71) Applicant: Tesorai, Inc., San Diego, CA (US)

(72) Inventors: Maximilien Burq, San Diego, CA (US); Jure Zbontar, San Diego, CA (US); Peter Cimermancic, San Diego, CA (US)

(73) Assignee: Tesorai, Inc., San Diego, CA (US)

( * ) Notice: Subject to any disclaimer, the term of this patent is extended or adjusted under 35 U.S.C. 154(b) by 0 days.

(21) Appl. No.: 18/943,185

(22) Filed: Nov. 11, 2024

(65) Prior Publication Data

US 2025/0157568 A1    May 15, 2025

Related U.S. Application Data

(60) Provisional application No. 63/682,215, filed on Aug. 12, 2024, provisional application No. 63/597,505, filed on Nov. 9, 2023.

(51) Int. Cl.
  *G16B 15/00*    (2019.01)
  *G06N 3/0464*   (2023.01)
  (Continued)

(52) U.S. Cl.
  CPC .......... *G16B 15/00* (2019.02); *G06N 3/0464* (2023.01); *G16B 40/10* (2019.02); *G16B 40/20* (2019.02)

(58) Field of Classification Search
  CPC ........ G06N 3/048; G06N 3/045; G06N 3/047; G06N 3/08; G06N 7/01; G06N 20/10; G06N 3/02; G06N 3/042; G06N 3/082; G06N 3/088; G06N 5/022; G06N 20/00; G06N 3/044; G06N 3/0442; G06N 3/0455; G06N 3/049; G06N 3/084; G06N 5/01; G06N 5/02; G16B 40/10; G16B 45/00;
  (Continued)

(56) References Cited

U.S. PATENT DOCUMENTS 10,705,100 B1 * 7/2020 Hansen ................. G01N 33/92
11,629,384 B2    4/2023 Batenchuk et al.
(Continued)

FOREIGN PATENT DOCUMENTS

CN    118155746 A    6/2024

OTHER PUBLICATIONS

Modeling Lower-Order Statistics to Enable Decoy-Free FDR Estimation in Proteomics Madej et al Published: Mar. 24, 2023 (Year: 2023).*

(Continued)

*Primary Examiner* — Luis A Sitiriche
(74) *Attorney, Agent, or Firm* — Jeffrey Schox; Annabel Imbrie-Moore

(57) ABSTRACT

The method for processing experimental data can include: determining experimental data (e.g., mass spectrometry spectra) and processing the experimental data. In variants, processing the experimental data can include: identifying one or more molecules, comparing experimental samples, determining a quantification, evaluating a quality of the experimental data, and/or otherwise processing the experimental data. The method can optionally include determining supplemental information, determining a set of candidate molecules, training a model, and/any other suitable steps.

19 Claims, 35 Drawing Sheets

(51) Int. Cl.
*G16B 40/10* (2019.01)
*G16B 40/20* (2019.01)

(58) Field of Classification Search
CPC ........ G16B 40/00; G16B 20/00; G16B 40/20;
G16B 15/00; G16B 25/00; G16B 5/00;
G16B 5/20; G16B 25/10; G16B 30/00;
G16B 50/00; G16B 15/30; G16B 20/50;
G16B 25/20; G16B 35/10; G16B 5/10;
G16B 50/10; G16B 50/30; G16H 10/40;
G16H 40/40

See application file for complete search history.

(56) References Cited

U.S. PATENT DOCUMENTS

| | | | |
|---|---|---|---|
| 11,862,298 B1 | 1/2024 | Palaniappan et al. | |
| 2019/0302054 A1* | 10/2019 | Bleiholder | G01N 27/623 |
| 2020/0392178 A1* | 12/2020 | Manica | G06N 3/084 |
| 2021/0215685 A1* | 7/2021 | Xia | G01N 33/54326 |
| 2021/0233640 A1* | 7/2021 | Banchereau | G06N 7/01 |
| 2022/0208540 A1* | 6/2022 | Behsaz | G06N 3/045 |
| 2023/0080329 A1* | 3/2023 | Liu | G06N 3/0464 |
| | | | 382/133 |
| 2023/0245439 A1 | 8/2023 | Batenchuk et al. | |
| 2024/0207626 A1* | 6/2024 | Tiwary | G06N 3/09 |

OTHER PUBLICATIONS

Some recommendations for multi-arm multi-stage trials Wason et al Statistical Methods in Medical Research 2016, vol. 25(2) 716-727 (Year: 2016).*

Litsa, et al., "An End-to-End Deep Learning Framework for Translating Mass Spectra to De-Novo Molecules", Communications Chemistry, Jun. 23, 2023, vol. 6, Article 132, [retrieved online Jan. 4, 2025]. <See Entire Document.>; Retrieved from [DOI: https://doi.org/ 10.1038/s42004-023-00932-3]; pp. 1-12.

Zheng, et al., "A BERT-Based Pretraining Model for Extracting Molecular Structural Information from a SMILES Sequence", ournal of Cheminformatics, Jun. 19, 2024, vol. 16, Article 71, [retrieved online Feb. 26, 2025]. Retrieved from [DOI: https://doi.org/10.1186/ sl33 21-024-00848-7]. pp. 1-9.

Zhou, et al., "S-MolSearch: 3D Semi-supervised Contrastive Learning for Bioactive Molecule Search", In: The Thirty-Eighth Annual Conference on Neural Information Processing Systems. Vancouver, Canada: NeurIPS 2024, Sep. 25, 2024, [retrieved online Feb. 26, 2025]. Retrieved from [URL: https://openreview.neUforum?id=wJAF8TGVUG]; pp. 1-23.

Altenburg, et al., "yHydra: Deep Learning enables an Ultra Fast Open Search by Jointly Embedding MS/MS Spectra and Peptides of Mass Spectrometry-based Proteomics", bioRxiv, https://www.biorxiv.org/content/10.1101/2021.12.01.470818v2, Dec. 11, 2021.

Ananth, et al., "A learned score function improves the power of mass spectrometry database search", bioRxiv, https://www.biorxiv.org/content/10.1101/2024.01.26.577425v2, Feb. 7, 2024.

Bassani-Sternberg, et al., "Direct identification of clinically relevant neoepitopes presented on native human melanoma tissue by mass spectrometry", Nature Communications, Nov. 21, 2016.

Bekker-Jense, et al., "An Optimized Shotgun Strategy for the Rapid Generation of Comprehensive Human Proteomes", Cell Systems, 4, pp. 587-599, Jun. 28, 2017.

Bittremieux, et al., "A learned embedding for efficient joint analysis of millions of mass spectra", Nat. Methods, 19(6) pp. 675-678, Jun. 2022.

Brown, et al., "Language Models are Few-Shot Learners", arXiv:2005.14165, Jul. 22, 2020.

Butler, et al., "MS2Mol: A transformer model for illuminating dark chemical space from mass spectra", ChemRxiv, Sep. 5, 2023, Version 4.

Cox, et al., "MaxQuant enables high peptide identification rates, individualized p.p.b.-range mass accuracies and proteome-wide protein quantification", Nature Biotechnology, vol. 26, No. 12, Dec. 2008.

Eng, et al., "An Approach to Correlate Tandem Mass Spectral Data of Peptides with Amino Acid Sequences in a Protein Database", Journal of the American Society for Mass Spectrometry, vol. 5, Issue 11, Nov. 1, 1994.

Freestone, et al., "Re-investigating the correctness of decoy-based false discovery rate control in proteomics tandem mass spectrometry", bioRxiv, https://doi.org/10.1101/2023.06.21.546013, Jun. 24, 2023.

Freestone, et al., "Reinvestigating the Correctness of Decoy-Based False Discovery Rate Control in Proteomics Tandem Mass Spectrometry", Journal of Proteome Research, 2024, 23, 1907-1914.

Freestone, et al., "Semi-supervised learning while controlling the FDR with an application to tandem mass spectrometry analysis", bioRxiv, https://www.biorxiv.org/content/10.1101/2023.10.26.564068v3, Jan. 26, 2024.

Gabriel, et al., "Prosit-TMT: Deep Learning Boosts Identification of TMT-Labeled Peptides", Anal. Chem., 2022, 94, 7181-7190.

Gessulat, et al., "Prosit: proteome-wide prediction of peptide tandem mass spectra by deep learning", Nature Methods, vol. 16, pp. 509-518, Jun. 2019.

Griss, Johannes, "Recognizing millions of consistently unidentified spectra across hundreds of shotgun proteomics datasets", Nature Methods, vol. 13, No. 8, Aug. 2016.

Jiang, et al., "The Future of Proteomics is Up in the Air: Can Ion Mobility Replace Liquid Chromatography for High Through put Proteomics?", Journal of Proteome Research, 2024, 23, 1871-1882.

Kall, et al., "Semi-supervised learning for peptide identification from shotgun proteomics datasets", Nature Methods, vol. 4, No. 11, Nov. 2007.

Keller, et al., "Empirical Statistical Model to Estimate the Accuracy of Peptide Identifications Made by MS/MS and Database Search", Analytical Chemistry, vol. 74, No. 20, Oct. 15, 2002.

Kim, et al., "MS-GF + makes progress towards a universal database search tool for proteomics", Nature Communications, Oct. 31, 2014.

Kleikamp, et al., "Metaproteomics, metagenomics and 16S rRNA sequencing provide different perspectives on the aerobic granular sludge microbiome", Water Research, 246 (2023) 120700.

Klimek, et al., "The Standard Protein Mix Database: A Diverse Dataset to Assist in the Production of Improved Peptide and Protein Identification Software Tools", J Proteome Res. Jan. 2008; 7(1): 96-103.

Kong, et al., "MSFragger: ultrafast and comprehensive peptide identification in shotgun proteomics", Nat Methods. May 2017; 14(5): 513-520.

Lazear, Michaelr. , "Sage: An Open-Source Tool for Fast Proteomics Searching and Quantification at Scale", Journal of Proteome, 2023, 22, 3652-3659.

Meier, et al., "Online Parallel Accumulation-Serial Fragmentation (PASEF) with a Novel Trapped Ion Mobility Mass Spectrometer", Molecular & Cellular Proteomics, 17, 2534-2545, Dec. 2018.

Radford, et al., "Improving Language Understanding by Generative Pre-Training", Preprint 2018.

Radford, et al., "Language Models are Unsupervised Multitask Learners", OpenAI, https://cdn.openai.com/better-language-models/language_models_are_unsupervised_multitask_learners. pdf, 2019.

Radford, et al., "Learning Transferable Visual Models From Natural Language Supervision", arXiv:2103.00020v1, Feb. 26, 2021.

Radford, et al., "Robust Speech Recognition via Large-Scale Weak Supervision", arXiv:2212.04356v1, Dec. 6, 2022.

Schoenholz, et al., "Peptide-Spectra Matching from Weak Supervision", arXiv:1808.06576v2, Aug. 22, 2018.

Tiwary, et al., "High-quality MS/MS spectrum prediction for data-dependent and data-independent acquisition data analysis", Nature Methods, vol. 16, pp. 519-525, Jun. 2019.

Wang, et al., "Assembling the Community-Scale Discoverable Human Proteome", Cell Systems, 7, 412-421, Oct. 24, 2018.

(56) References Cited

OTHER PUBLICATIONS

Wen, et al., "Assessment of false discovery rate control in tandem mass spectrometry analysis using entrapment", bioRxiv, Jun. 4, 2024.

Wilhelm, et al., "Deep learning boosts sensitivity of mass spectrometry-based immunopeptidomics", Nature Communications, 12, Article No. 3346, Jun. 23, 2021.

Williams, et al., "Automated Coupling of Nanodroplet Sample Preparation with Liquid Chromatography-Mass Spectrometry for High-Throughput Single-Cell Proteomics", Anal Chem., Aug. 4, 2020; 92(15): 10588-10596.

\* cited by examiner

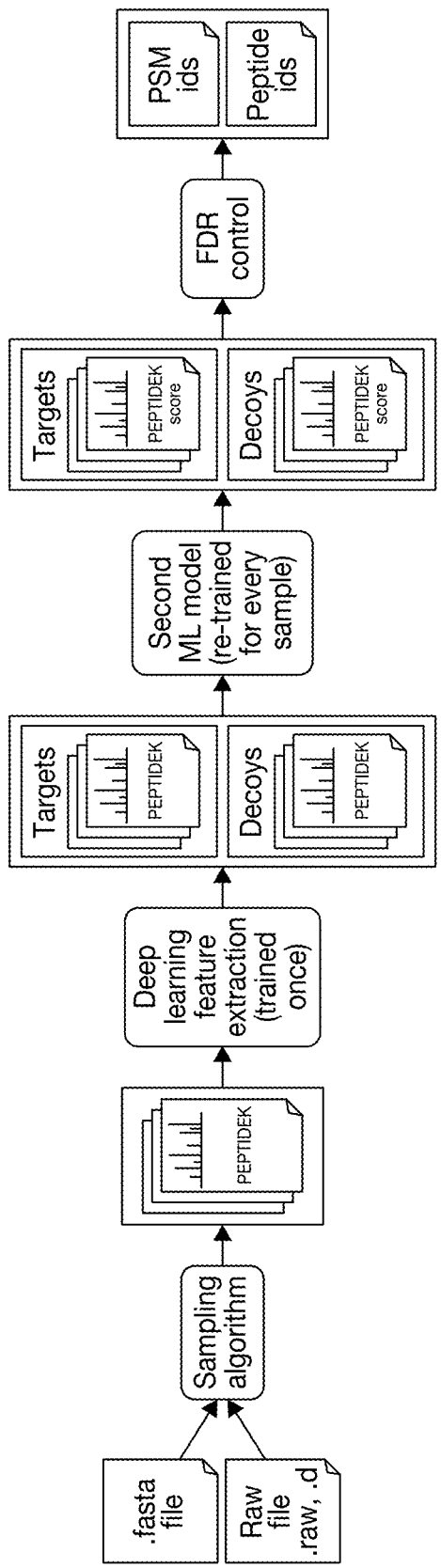
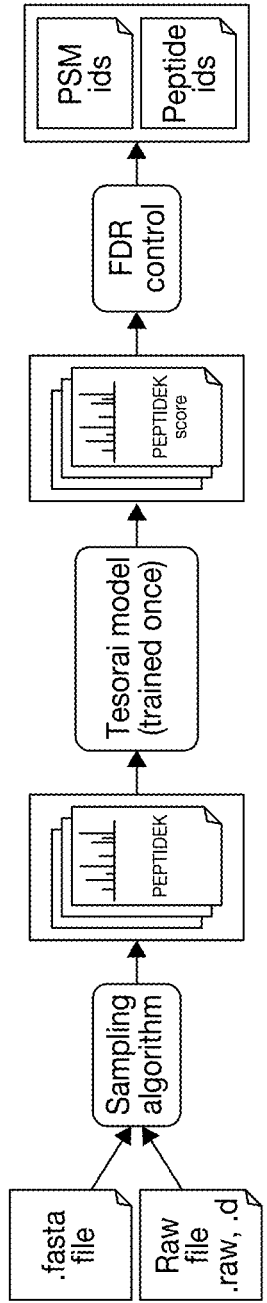
FIGURE 11A
FIGURE 11B

| | | |
|---|---|---|
| ← → C ◯ console.tesorai.com/createJob/ ☆ | | ⊕ ⇄ ⏐ ◯ Relaunch to update : |

Tesorai

- Home
- — Jobs
- Files
- Tokens
- FAQ

| Name | Size | Date |
|---|---|---|
| ☑ YE_20180428_SK_HLA_A0202_3lps_a50mio_R1_01.raw | 320.97 Mb | Sep 29 2024 |
| ☑ YE_20180517_SK_HLA_A1101_3lPs_a50mio_R1_01.raw | 301.46 Mb | Sep 29 2024 |
| ☑ MS20160409_CRH_HLA_B_2705_BioRep1_TechRep1.raw | 540.89 Mb | Sep 29 2024 |
| ☐ GG20161104_CRH_HLA_C0302_BioRep1_inject1.raw | 561.4 Mb | Sep 29 2024 |
| ☐ GG20161104_CRH_HLA_C1402_BioRep2_inject1.raw | 592.04 Mb | Sep 29 2024 |

Fasta files

| Select ▸ |
|---|
| ups1-ups2-sequences.fasta |
| UCP_uniprotkb_human_AND_model_organism_9606_2023_12-07.fasta |
| uniprotkb_taxonomy_id_3702_AND_reviewed_2024_05_22.fasta |

Total: 5 tokens

Your tokens: 93    + Add balance

[ Start job for 5 tokens ]

FIGURE 17C

| | | | | | |
|---|---|---|---|---|---|
| Jobs | | | | | + Start a job |
| Q Search | | | Filter by status ▸ | Filter by start date ▸ | |
| | Size | Files/Tokens | Status | Start time | Completed time  Duration |
| | 2.26 Gb | 5 | ⊙ Pending | Sep 30, 10:12 pm | 0h 0min |
| | 2.26 Gb | 5 | △ Finished | Sep 29, 09:15 pm | Sep 30, 12:23 am  3h 8min |
| | 1.51 Gb | 2 | △ Finished | Sep 07, 07:29 am | Sep 07, 09:53 am  2h 24min |
| | 1.45 Gb | 2 | △ Finished | Sep 07, 07:28 am | Sep 07, 08:11 am  0h 42min |
| | 769.32 Mb | 1 | △ Finished | Jul 08, 08:47 pm | Jul 08, 09:23 am  0h 35min |
| | 1.76 Gb | 1 | △ Finished | Jun 27, 10:23 pm | Jun 27, 10:51 pm  0h 27min |
| | 1.76 Gb | 2 | △ Finished | Jun 10, 07:43 pm | Jun 10, 08:19 pm  0h 35min |
| | 1.45 Gb | 2 | △ Finished | Jun 04, 05:05 pm | Jun 04, 05:43 pm  0h 38min |
| | 1.51 Gb | 2 | △ Finished | May 30, 07:00 am | May 30, 09:20 pm  2h 20min |
| | 374.19 Mb | 1 | △ Finished | May 22, 06:35 am | May 22, 06:55 am  0h 20min |

FIGURE 17E

SYSTEM AND METHOD FOR PROCESSING EXPERIMENTAL DATA

CROSS-REFERENCE TO RELATED APPLICATIONS

This application claims the benefit of U.S. Provisional Application No. 63/597,505 filed 9 Nov. 2023 and U.S. Provisional Application No. 63/682,215 filed 12 Aug. 2024, each of which is incorporated in its entirety by this reference.

TECHNICAL FIELD

This invention relates generally to the molecular data analysis field, and more specifically to a new and useful system and method for processing experimental in the molecular data analysis field.

BRIEF DESCRIPTION OF THE FIGURES

FIG. 11A is a schematic representation of a second-generation semi-supervised ML tool.

FIG. 11B is a schematic representation of an example of the molecule identification model ("Tesorai").

FIGS. 17A-17K depict illustrative examples of a user interface.

DETAILED DESCRIPTION

The following description of the embodiments of the invention is not intended to limit the invention to these embodiments, but rather to enable any person skilled in the art to make and use this invention.

1. Overview

Figure 1:
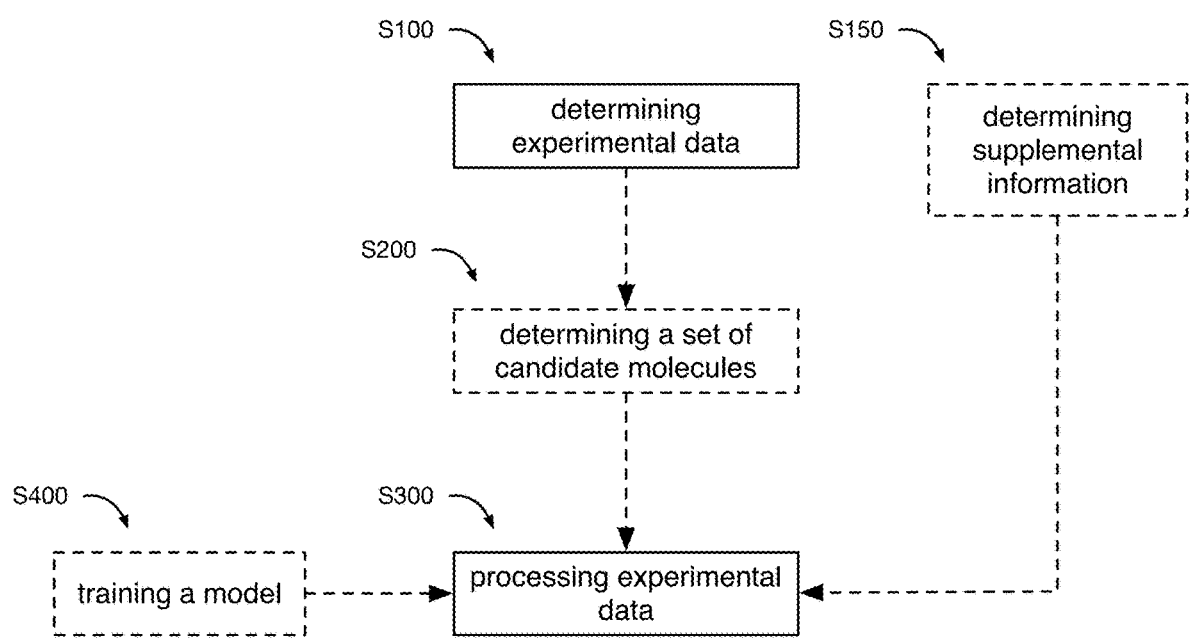
FIG. 1 is a schematic representation of a variant of the method.

As shown in FIG. 1, the method can include: determining experimental data S100 and determining processed experimental data S300. However, the method can additionally or alternatively include any other suitable steps.

In variants, the method can function to process (e.g., preprocess) experimental data (e.g., mass spectrometry data). In examples, the method can be used for standard trypsin-digested human samples, single-cell and isobaric-labeled samples, proteomics, metabolomics, transcriptomics, genomics, epigenetics, interactomics, protein/protein interactions, membrane permeability, immunopeptideomics, chemoproteomics, metaproteomics, and/or any other molecular analysis. In a first example, the method can function to identify and/or quantify molecules (e.g., peptides, small molecules, proteins, proteoforms, large molecules, etc.) present in a sample. In a second example, the method can function to perform a similarity analysis across samples. In a third example, the method can function to map sequences (e.g., RNA short-read sequence, DNA short-read sequence, peptide sequences, etc.) to a reference (e.g., reference transcriptome, reference genome, protein sequence, etc.). In a fourth example, the method can function to measure quality of the experimental data (e.g., immediately after acquisition).

2. Examples

In a first example, the method can include: receiving a mass spectrometry spectrum for a molecule of interest; determining an embedding for the spectrum using an experimental data encoder; determining an embedding for each candidate molecule in a set of candidate molecules using a molecule encoder; and, for each candidate molecule, outputting a score (e.g., a likelihood that the molecule of interest matches the candidate molecule) using a scoring model. The method can optionally include determining a subset of the candidate molecules (e.g., identifying the highest scoring candidate molecule) and/or ranking candidate molecules. In specific examples, the candidate molecules can be peptides (e.g., modified and/or unmodified peptides), small molecules, and/or any other molecules. The molecule encoder and/or the scoring model can optionally take in supplementary information such as context parameters (e.g., type of mass spectrometry system, digestion enzyme, amino-acid modifications, etc.), additional experimental data (e.g., retention times, ion mobility, etc.), and/or other information. In an illustrative example, the method can include identifying a set of peptides of interest (e.g., a peptide for each spectrum in a set of mass spectrometry data) and/or identifying proteins (e.g., generating a protein expression table) based on the identified peptides of interest.

In a second example, the method can include: receiving mass spectrometry spectra for a first sample and a second sample; determining an embedding for each spectrum using an experimental data encoder; and performing a similarity analysis (e.g., using clustering analysis) based on the embeddings. In a specific example, the similarity analysis can be used on samples of multiple-arm experiment (e.g., a control sample and a treated sample), wherein the similarity analysis is used to identify embedding(s) of interest (e.g., embeddings corresponding to spectra differentially present in only one of the two samples). The embedding(s) of interest can optionally be matched to a candidate molecule using a scoring model (e.g., as described above).

3. Technical Advantages

Variants of the technology can confer one or more advantages over conventional technologies.

First, current preprocessing systems functioning locally on workstations discard significant amounts of experimental data. Variants of the technology can retain more of the experimental data (e.g., at least 50% of the data, at least 75%, at least 90%, etc.) during preprocessing, which can enable improved accuracy and/or improved downstream processing (e.g., by using information in the additional retained data). For example, variants of the technology can perform molecule identification, quantification, quality evaluation, and/or comparisons between experimental samples, using an embedding to represent a mass spectrometry spectrum, wherein the embedding retains a greater portion of the underlying information within the mass spectrometry spectrum (e.g., including intensity information) and/or retains a greater portion of the important information (relevant to the preprocessing task) within the mass spectrometry spectrum.

Second, variants of the technology can perform molecule identification (e.g., peptide-spectrum matching) and/or other experimental data preprocessing with increased speed. In an example, the use of cloud-based processing with parallel computing (e.g., parallel candidate molecule scoring) can increase computational efficiency. This increased speed can enable the use of more advanced algorithms, thus increasing the number of candidate molecules that can be evaluated and/or an increased amount of data that can be retained. In another example, the molecule identification model can use deep learning encoders that feed into a shallow scoring model (e.g., calculating a Euclidean distance), which can speed up the molecule identification computation time relative to using a deep learning scoring model (e.g., from $O(n^2)$ to $O(n)$).

Third, variants of the technology can identify net new proteins, proteoforms, and/or other analytes in a sample that current systems would miss. In a specific example, increased accuracy in molecule identification (e.g., matching a spectrum to a peptide) can increase the statistical power to identify additional candidate molecules in multiple hypothesis testing, which can allow for a larger list of peptides and/or molecules to be searched against, and an increase in the number of candidate molecules that can be evaluated. This increased number of candidate molecules that are evaluated can increase the number of identified molecules in a sample. In an illustrative example, the method can increase the number of identified molecules relative to a standard matching process (e.g., MaxQuant). Examples are shown in FIGS. 13A-13G, FIG. 14A, and FIG. 14B.

Fourth, current systems preprocess a single type of experimental data (e.g., data for a single mass spectrometry acquisition mode). Variants of the technology can preprocess multiple types of experimental data (e.g., proteomics data, metabolomics data, transcriptomics data, genomics data, epigenetic data, etc.), multiple acquisition modes (e.g., DDA, DIA, TMT, etc.), and/or other experimental data. For example, a single model (e.g., a molecule identification model and/or an experimental data encoder therein) can receive data of varying dimensions (e.g., 1 dimension, 2 dimensions, 3 dimensions, 4 dimensions, etc.) corresponding to different experimental data acquisition modes.

Figure 12B:
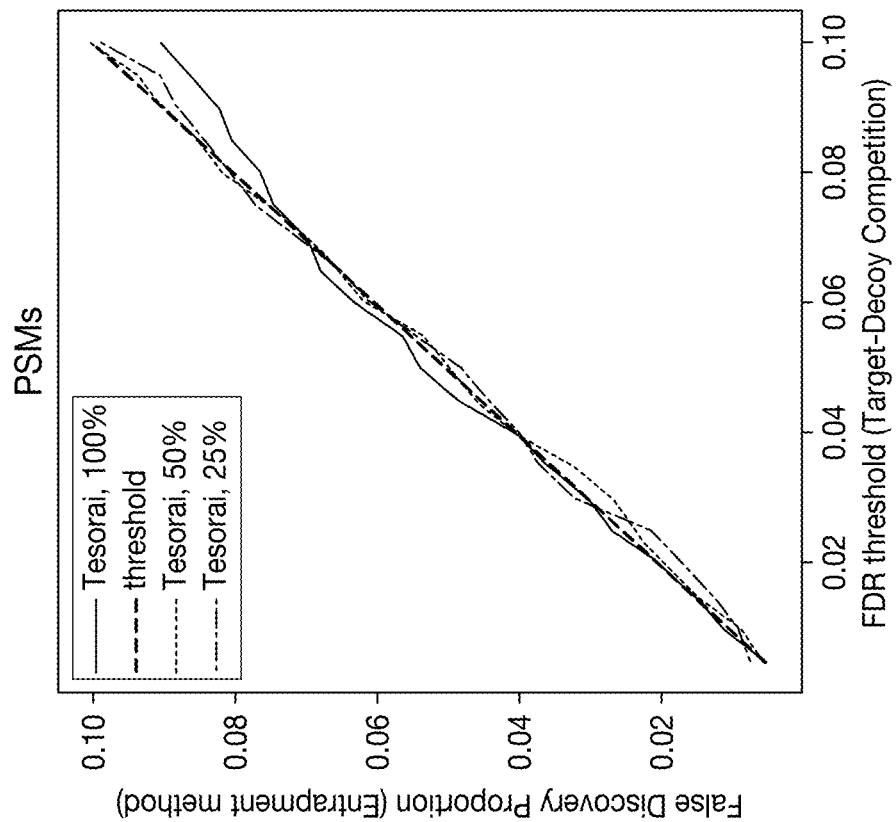
FIGS. 12A and 12B depict false discovery rate (FDR) calibration results for an example of the molecule identification model ("Tesorai"), showing the false-discovery proportion (e.g., determined using an entrapment method) as a function of false-discovery threshold (e.g., estimated using target-decoy competition) for peptide-spectrum matches (PSM) and for peptides.
Figure 12A:
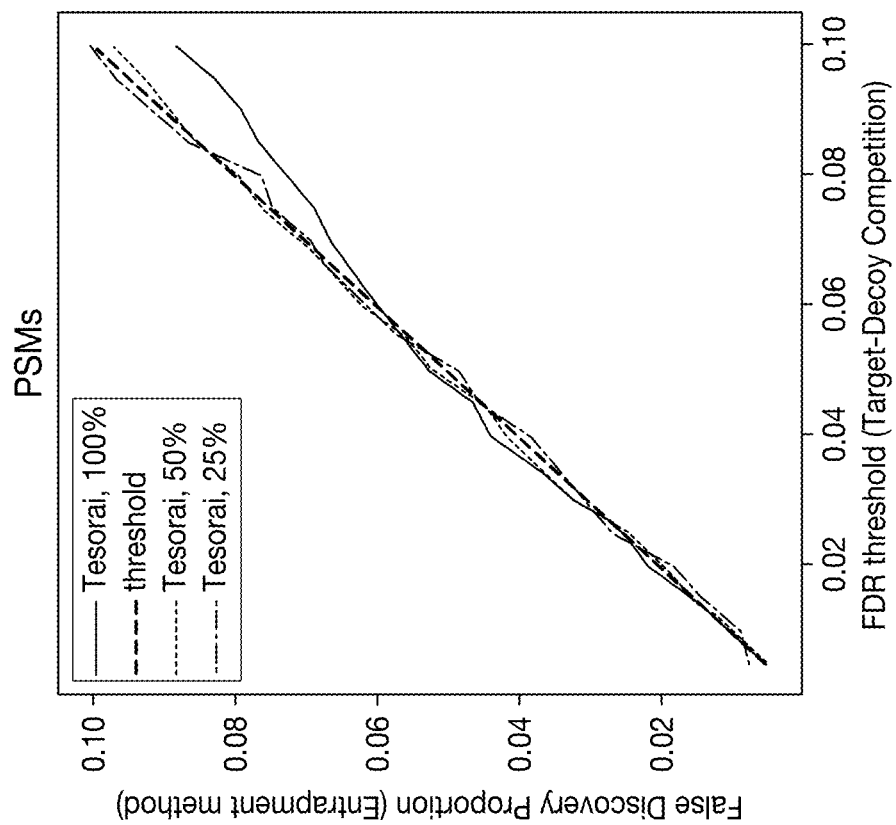
Figure 13A:
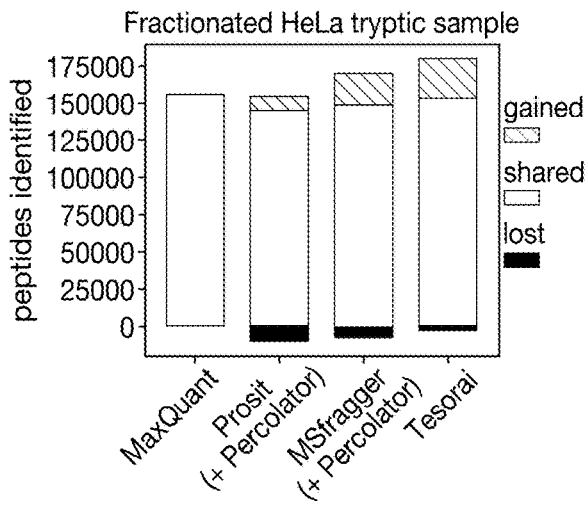
FIGS. 13A-13G depict example peptide identifications at a 1% false discovery rate (FDR) for three models of interest compared to the peptides identified by MaxQuant. The models of interest include: Prosit, MSFragger, and an example of the molecule identification model ("Tesorai"). "Shared" indicates peptides identified by both MaxQuant and the model of interest; "Gained" indicates new identifications; "Lost" indicates peptides identified by MaxQuant only.
Figure 13B:
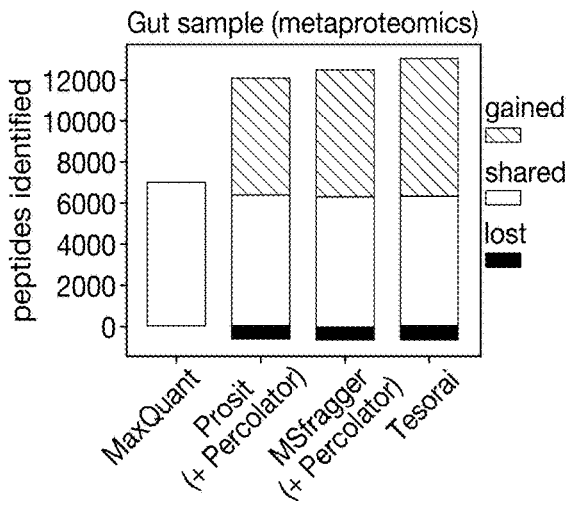
Figure 13C:
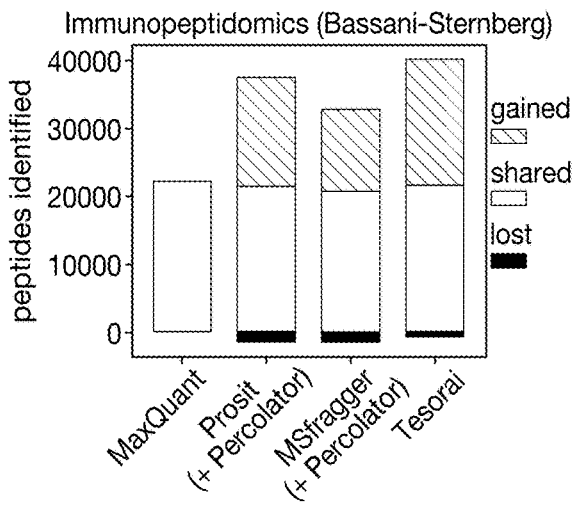
Figure 13D:
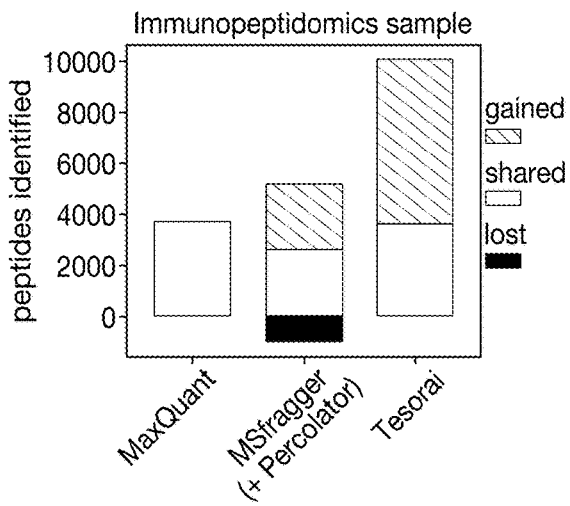
Figure 13E:
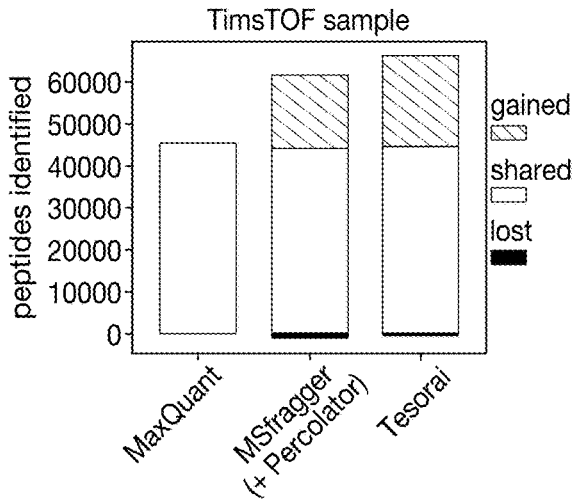
Figure 13F:
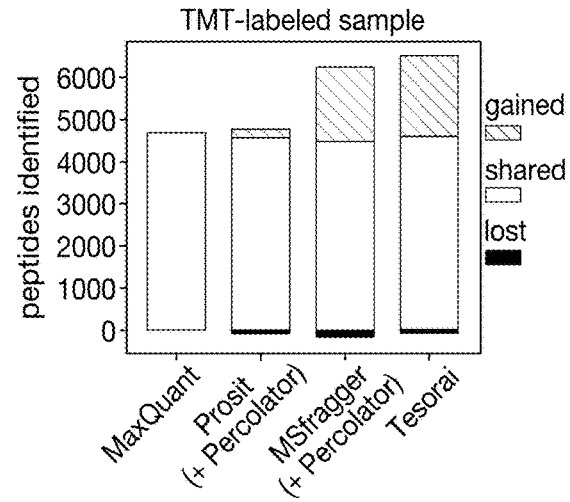
Figure 13G:
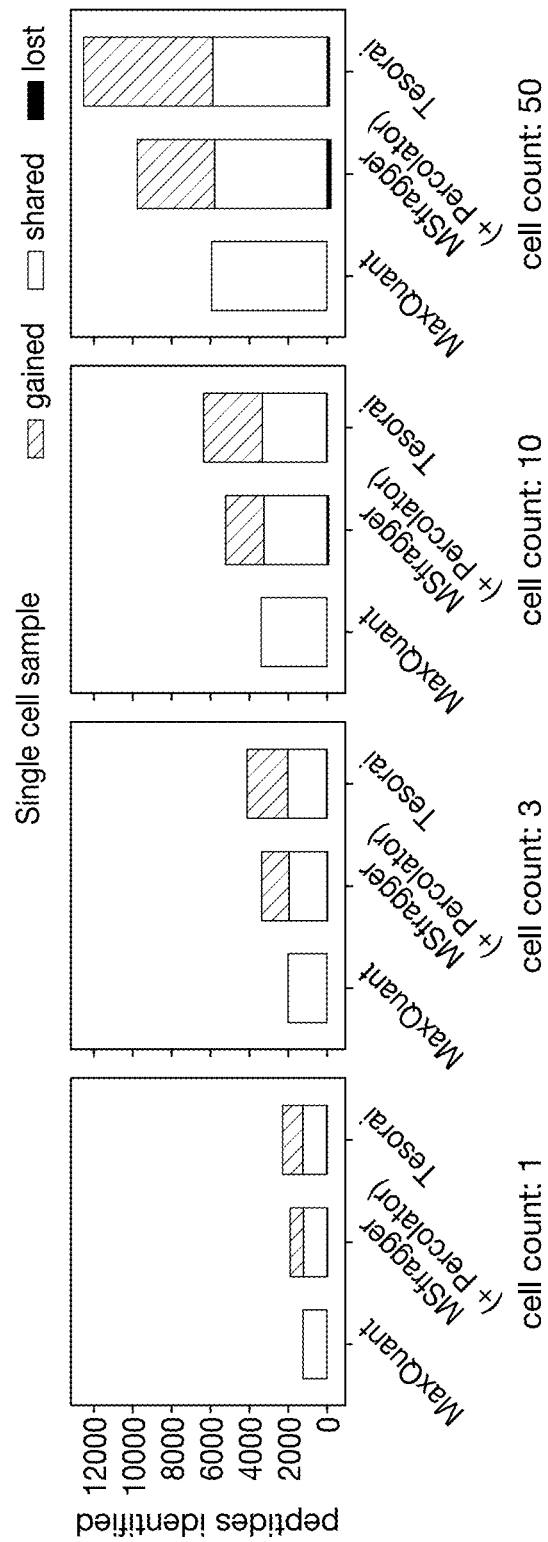
Figure 14A:
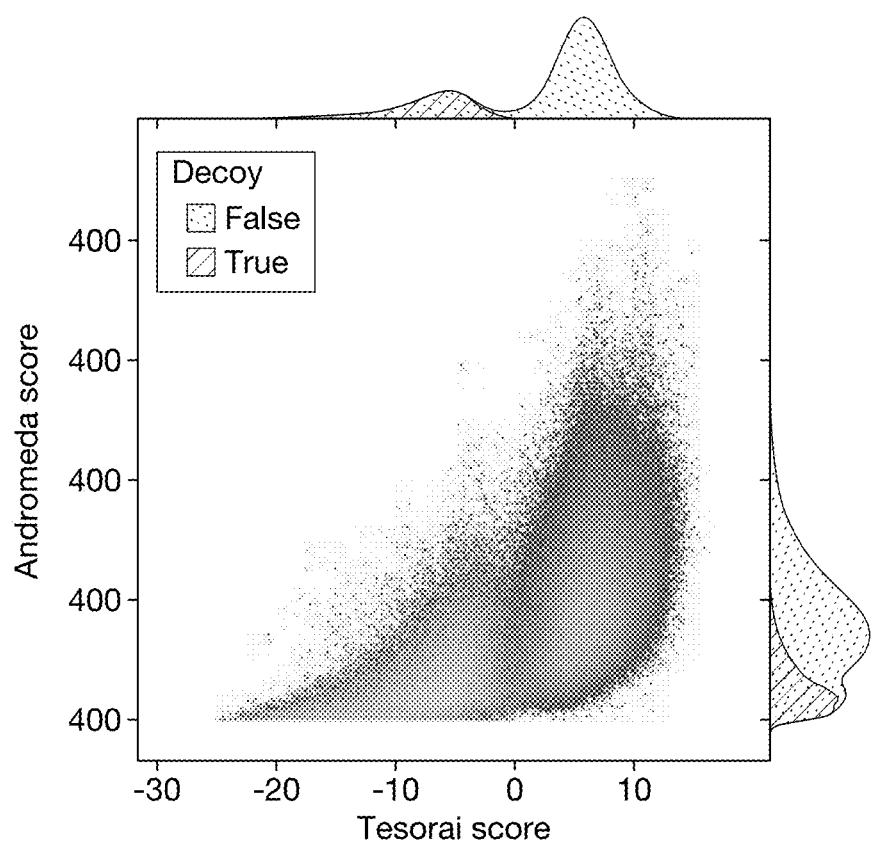
FIG. 14A depicts an example of a joint distribution of the Andromeda score from MaxQuant, against the score from an example of the molecule identification model ("Tesorai").
Figure 14B:
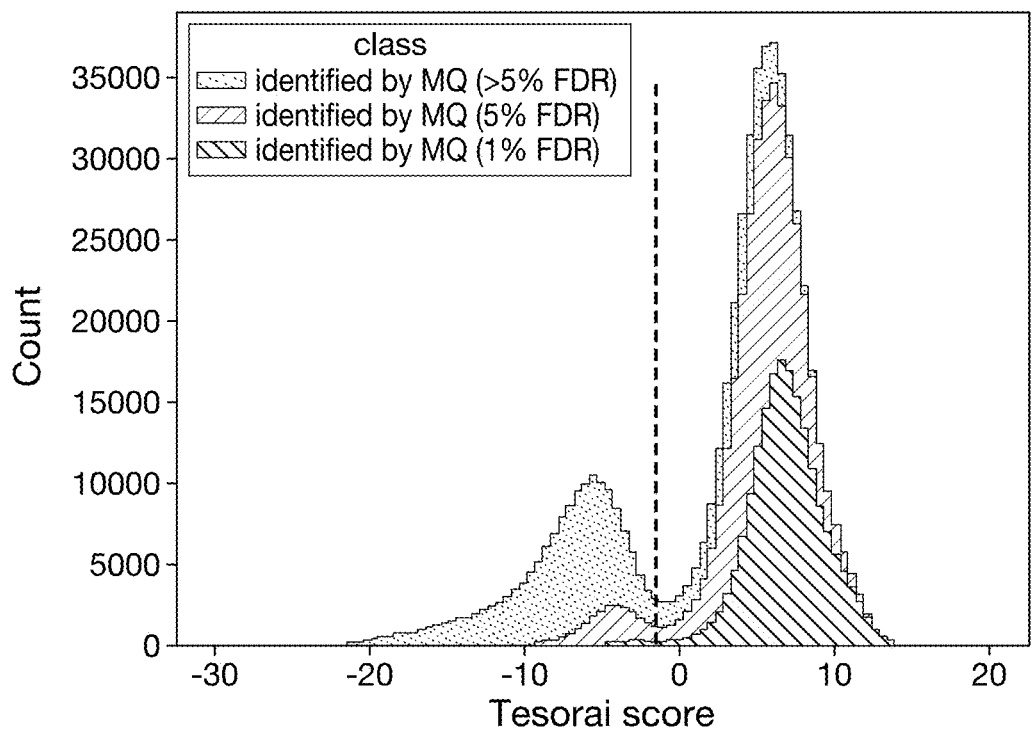
FIG. 14B depicts an example breakdown of peptide-spectrum matches (PSMs) identified using the example of the molecule identification model ("Tesorai") by whether they also were identified by MaxQuant at various false discovery rate (FDR) thresholds. The dashed line represents a 1% FDR cutoff for the molecule identification model score.

Fifth, current database search algorithms for mass spectrometry proteomics typically fail to identify up to 75% of spectra. To mitigate the issue, tools such as Percolator and PeptideProphet leverage machine learning for rescoring. Though this can boost peptide and protein identification rates, the fact that they are trained to separate targets from decoys can lead to inaccurate false-discovery rate (FDR) estimates. In particular, their dual use of decoys—both for training its machine learning model and estimating the FDR—can inadvertently lead to overfitting and insufficient FDR control. Variants of the technology described herein can include a pre-trained large deep learning molecule identification model that can take the raw spectrum and peptide sequence as input, directly outputting a score that effectively distinguishes correct from incorrect peptide-spectrum matches-without requiring retraining on each new sample, and/or without ever seeing decoys during training. In variants, this can ensure that real sequences are in the positive and in the negative classes, which can prevent the model from memorizing the entire peptidomes of the species included in the training set. In a specific example, this method can enable estimating the ability of the molecule identification model to accurately estimate FDR even in the case where the correct target sequence is not in the search set (e.g., examples shown in FIG. 12A and FIG. 12B).

Sixth, variants of the technology can greatly simplify experimental data processing by removing the need for custom steps such as spectrum de-isotoping, charge correction, or score recalibration.

However, further advantages can be provided by the system and method disclosed herein.

4. System

The method can be performed using a system including a computing system. The system can optionally include and/or interface with: a database, user interface, assay tools, and/or any other suitable components.

The computing system can include one or more: CPUs, GPUs, TPUs, custom FPGA/ASICS, microprocessors, servers, cloud computing, and/or any other suitable components. The computing system can be local, remote (e.g., cloud computing server, etc.), distributed, and/or otherwise arranged relative to any other system or module. For example, the computing system can include a cloud platform (e.g., including one or more cloud computing servers). In variants, this cloud-based implementation can enhance the processing speed. In an example, a user can upload raw experimental data (e.g., raw spectral files and one or more corresponding database files) to the cloud platform, wherein all or a portion of the method can be performed on the cloud platform.

The system can optionally include or interface with a database, which can function to store candidate molecules (e.g., a "search database" of candidate molecules), unprocessed experimental data, processed experimental data, supplemental information, representations (e.g., embeddings), known matches between molecules and experimental data (e.g., spectral libraries), training data, model parameters (e.g., post-training), and/or any other information.

Figure 16A:
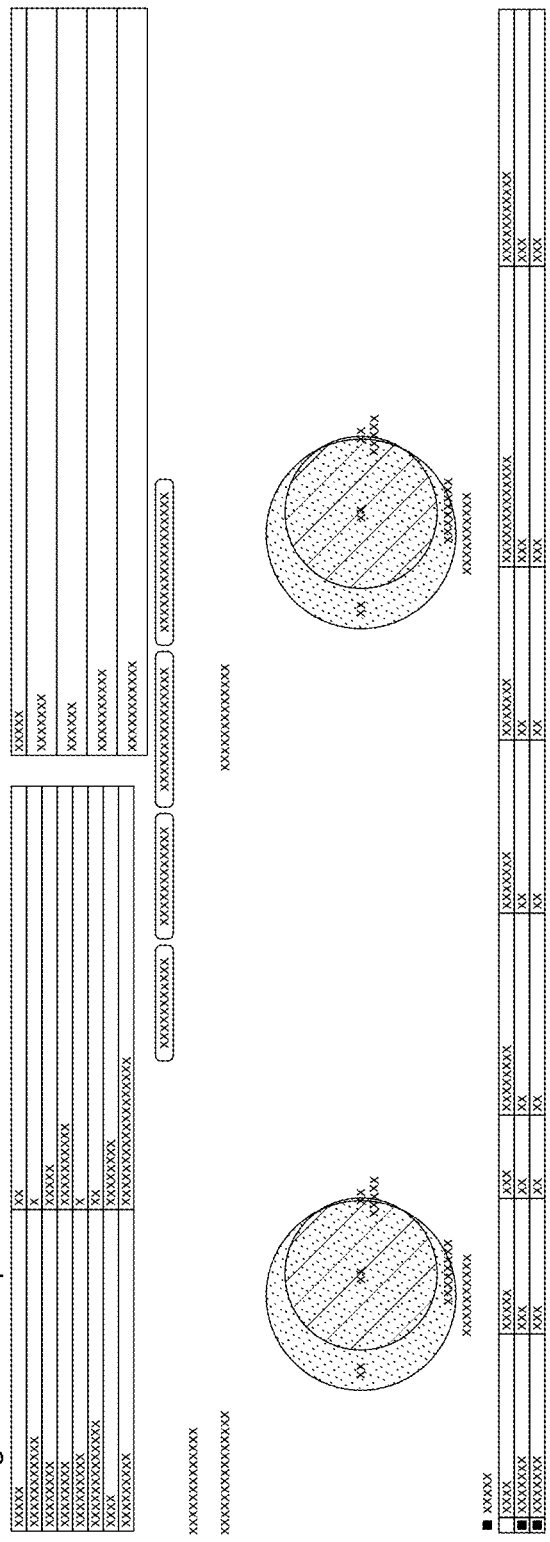
FIGS. 16A-16C depict illustrative examples of processed experimental data (e.g., reports) displayed at a user interface.
Figure 16B:
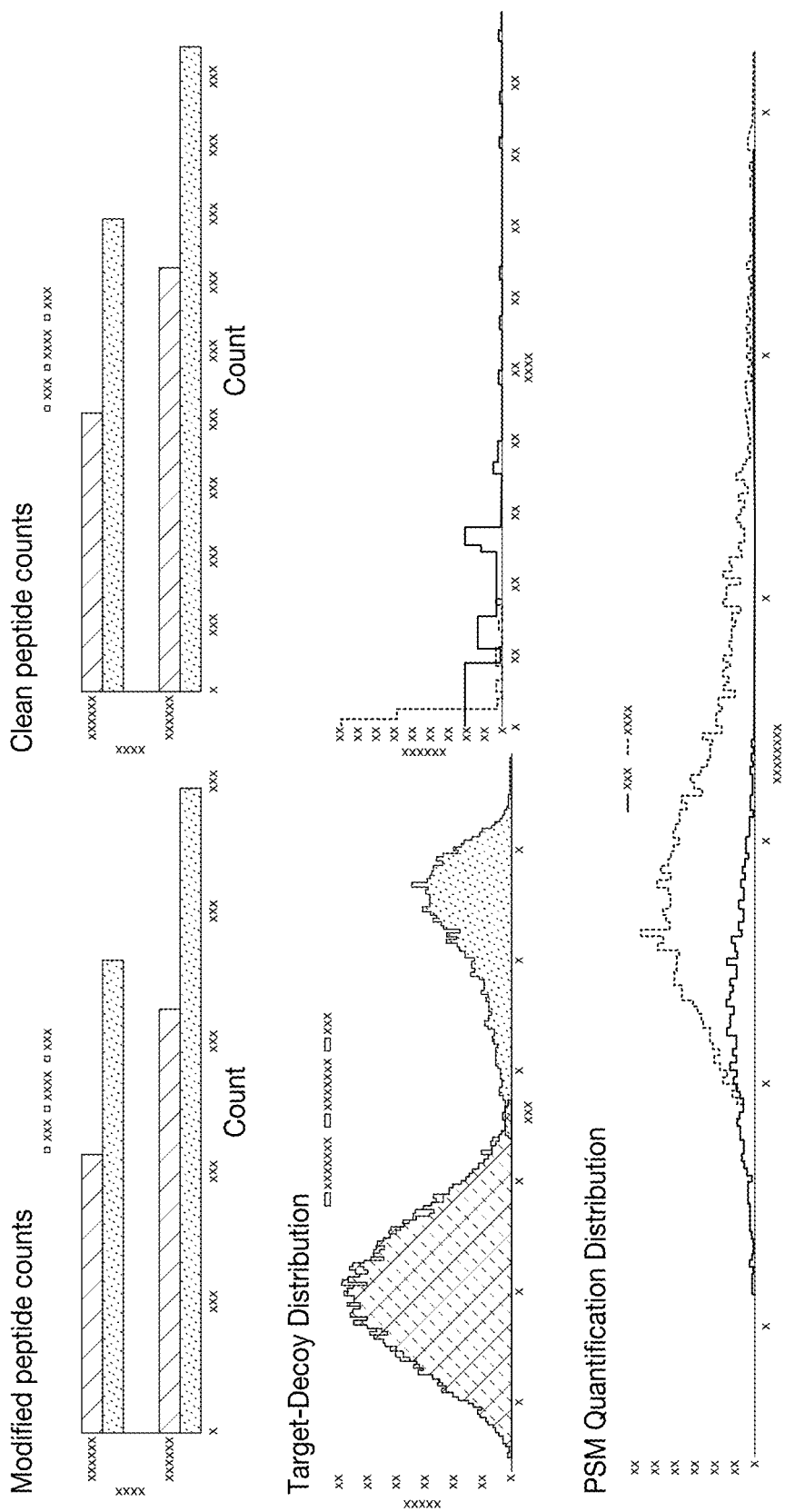
Figure 16C:
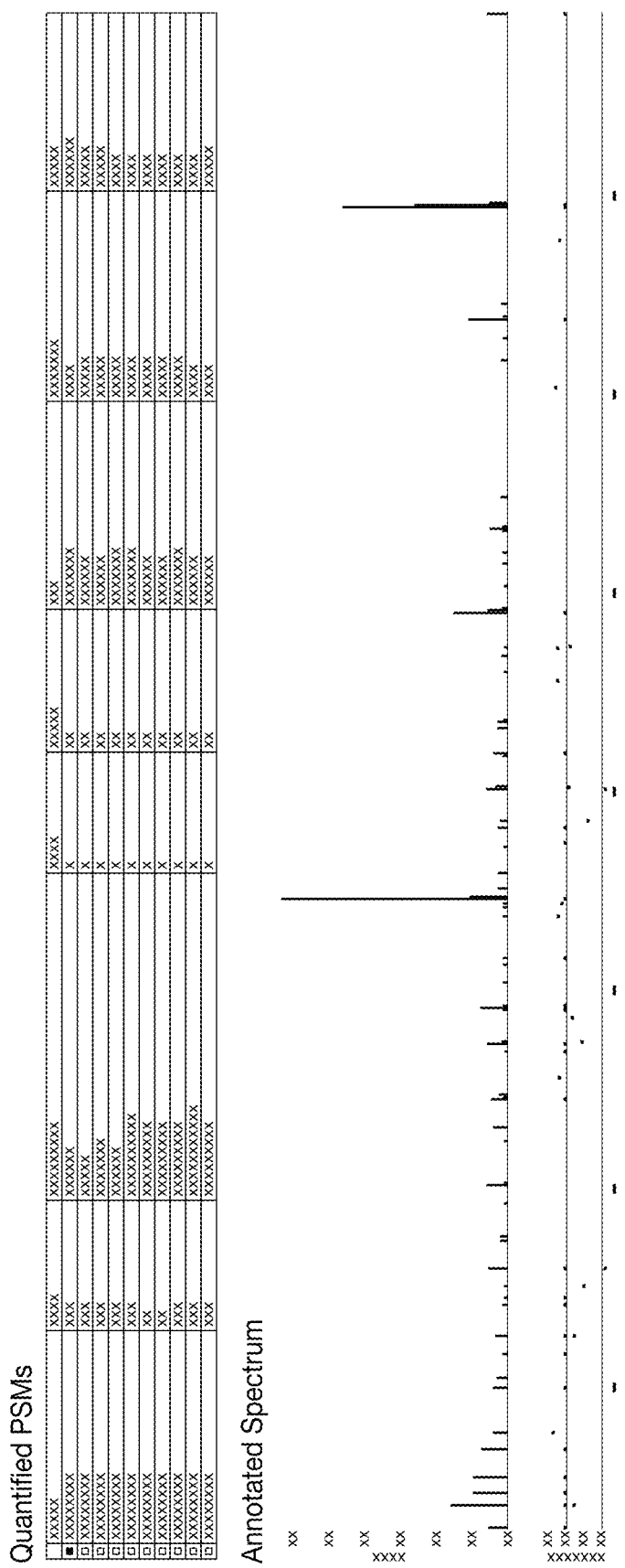
Figure 17A:
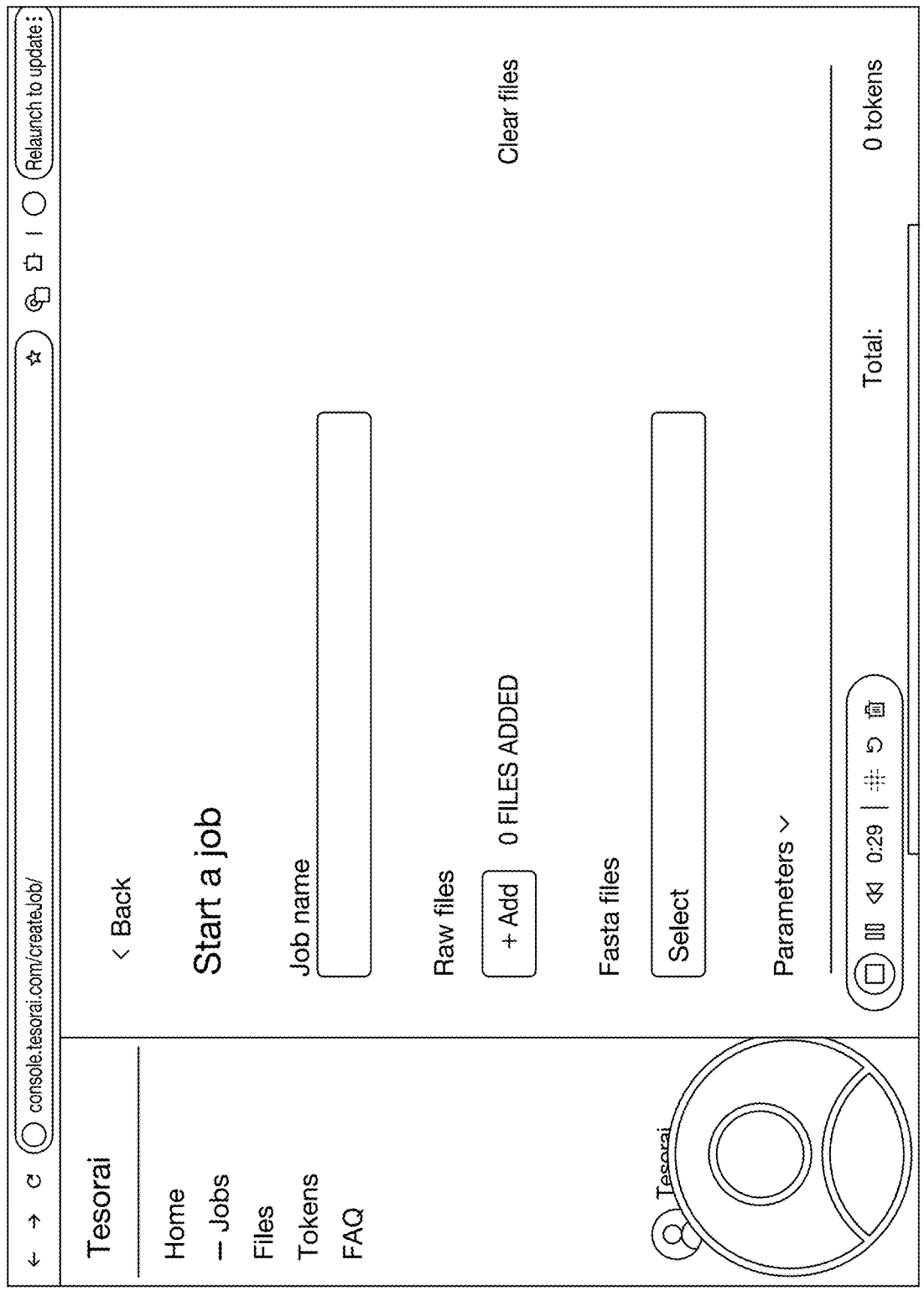
Figure 17B:
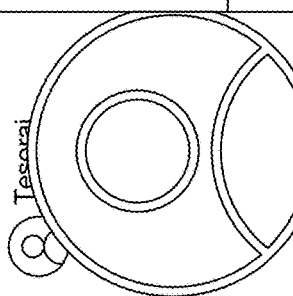
Figure 17D:
Figure 17F:
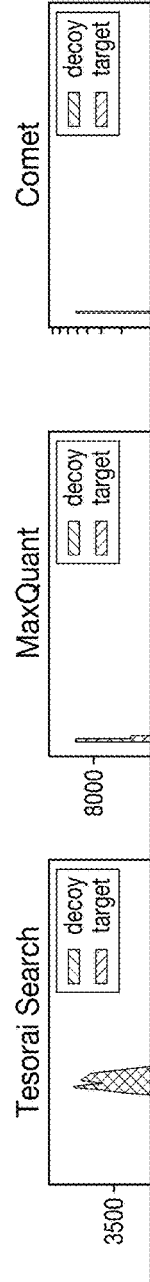
Figure 17G:
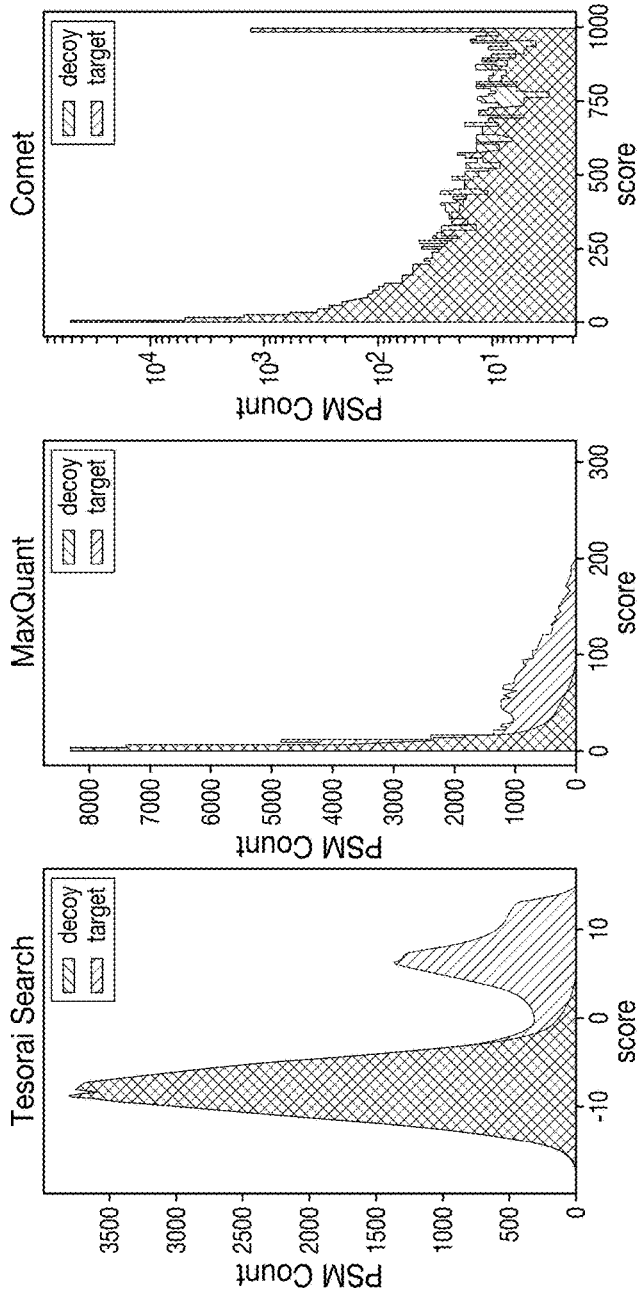
Figure 17H:
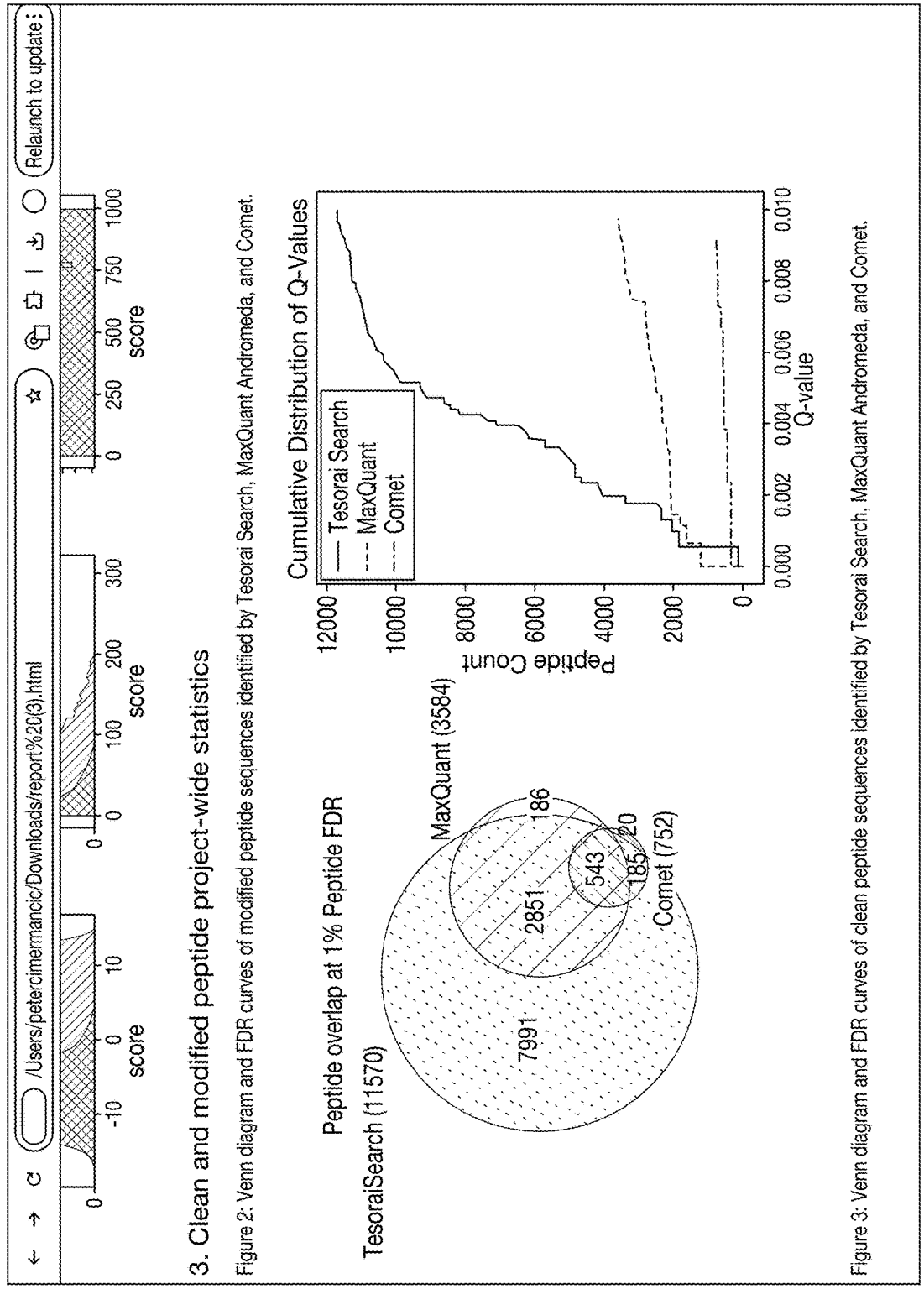
Figure 17I:
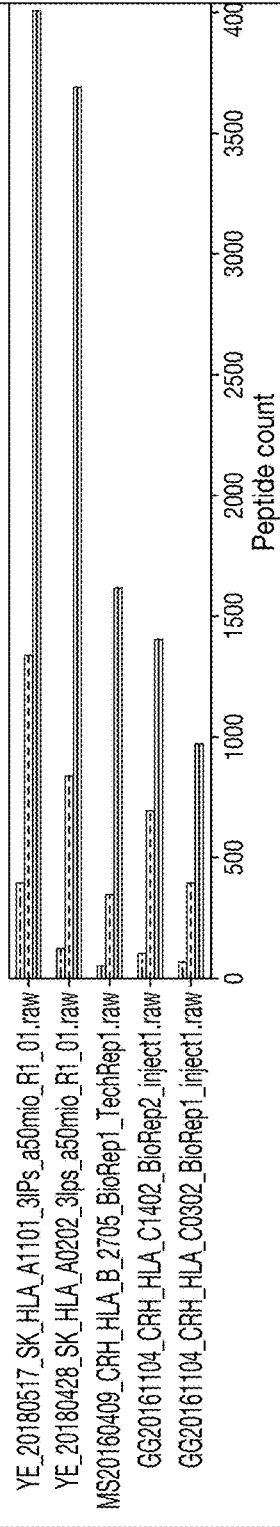
Figure 17I:
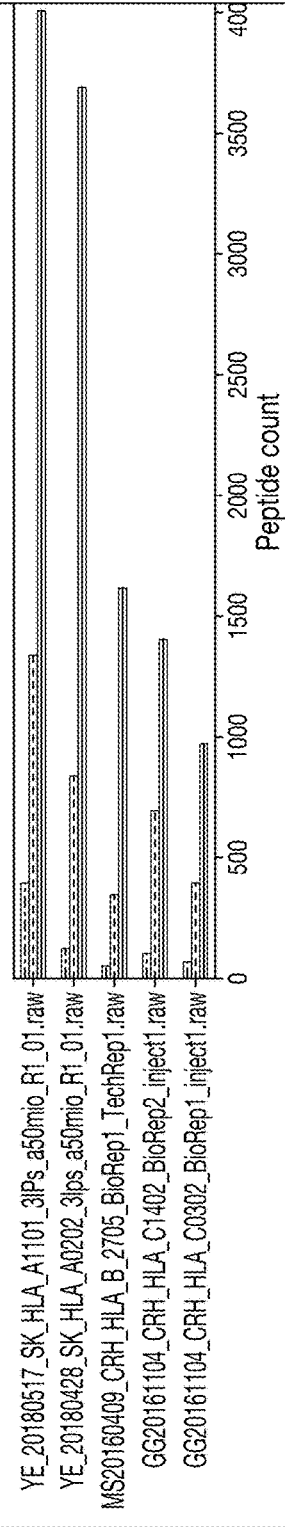
Figure 17I:
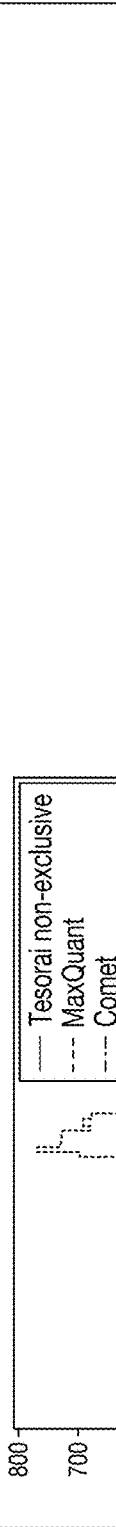
Figure 17J:
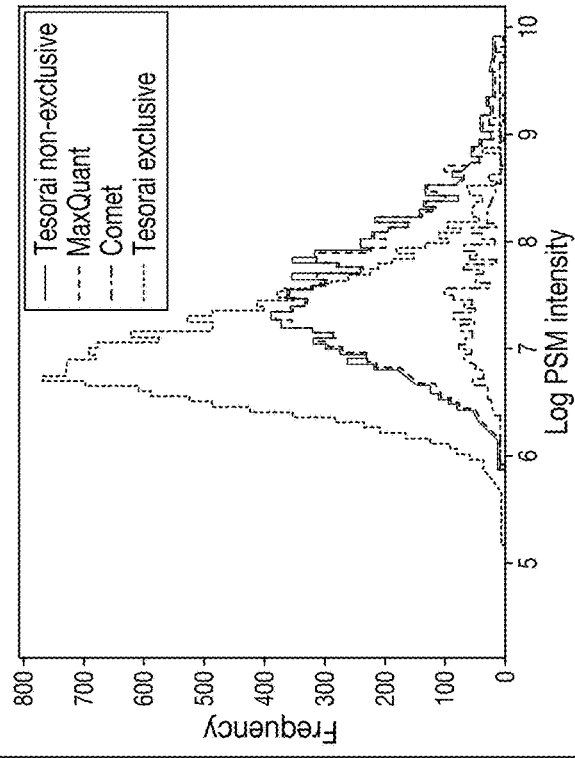
Figure 17K:
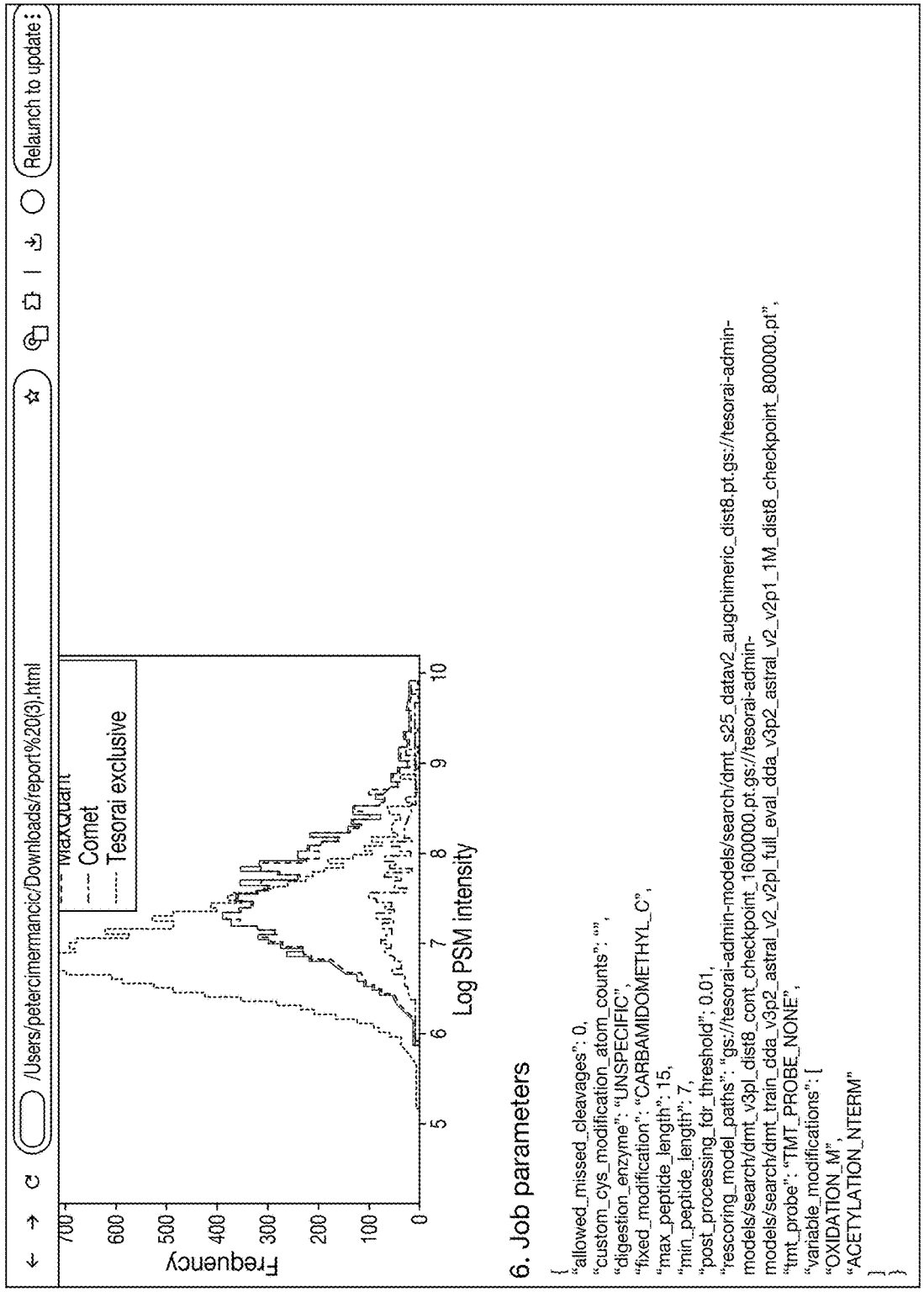

The system can optionally include or interface with a user interface, which can function to receive one or more inputs (e.g., from a user), display one or more outputs (e.g., model outputs), display any other parameters, and/or otherwise function. Examples are shown in FIGS. 17A-17K. In an example, the user interface can receive experimental data, supplemental information, candidate molecules (e.g., a search database), and/or any other information. In a specific example, the user interface can receive one or more spectral files (e.g., RAW files) and one or more corresponding search databases of candidate molecules (e.g., fasta files). In an example, the user interface can display processed experimental data. Examples are shown in FIG. 16A, FIG. 16B, and FIG. 16C. Specific examples of processed experimental data include: identified molecules (e.g., peptides, proteins, etc.), peptide identification tables, protein expression tables, quantification of a molecule, quality evaluation, scores, rankings (e.g., a ranking of candidate molecules), similarity analyses, loci (e.g., a locus of a post-translational modification), graphical displays (e.g., data diagnostic plots), a report, and/or any other processed experimental data. In a specific example, an identified molecule is a peptide-spectrum match (PSM).

The system can optionally include or interface with one or more assay tools (e.g., instruments), which can function to collect (e.g., measure) experimental data. Examples of assay tool types include: mass spectrometers (e.g., configured to perform a mass spectrometry assay), DNA/RNA sequencers, and/or any other assay tool. Examples of mass spectrometry assays include: liquid chromatography-mass spectrometry (LC-MS), time-of-flight mass spectrometry (TOF-MS), gas chromatography-mass spectrometry (GC-MS), capillary electrophoresis-mass spectrometry (CE-MS), ion mobility spectrometry-mass spectrometry (IMS-MS), selected-ion flow-tube mass spectrometry (SIFT-MS), fourier transform mass spectrometry (FT-MS), ion trap mass spectrometry (IT-MS), any other mass spectrometry assay, and/or any other suitable assays. Any mass spectrometry assay can optionally be a tandem mass spectrometry assay (e.g., liquid chromatography-tandem mass spectrometry (LC-MS/MS)). Examples of mass spectrometry (MS) modes that can be used to collect experimental data include: data-dependent acquisition (DDA), data independent acquisition (DIA), tandem mass tag (TMT), and/or any other MS method.

However, the system can be otherwise configured.

5. Method

As shown in FIG. 1, the method can include: determining experimental data S100 and processing experimental data S300. The method can optionally include determining supplemental information S150, determining a set of candidate molecules S200, training a model S400, and/any other suitable steps.

All or portions of the method can be performed by one or more components of the system, using a computing system, using a database (e.g., a system database, a third-party database, a search database, etc.), user interface, by a user, and/or by any other suitable system.

The method can be performed after experimental data has been collected, before downstream processing of the experimental data, before downstream experiments, and/or at any other time. All or portions of the method can optionally be iteratively performed (e.g., repeated for each candidate molecule in a set, repeated for each spectrum in a set of mass spectrometry spectra, repeated for each spectrum peak in a set of mass spectrometry spectra, repeated for each sample in a set of samples, etc.). All or portions of the method can be performed automatically, manually, semi-automatically, and/or otherwise performed.

5.1. Determining Experimental Data S100

Determining experimental data S100 functions to determine data for molecules within one or more samples. The experimental data preferably corresponds to an individual molecule of interest in a sample (e.g., a precursor), but can alternatively correspond to multiple molecules (e.g., all or a portion of the molecules in the sample). The molecule of interest can be a peptide (e.g., a modified peptide, an unmodified peptide, etc.), a small molecule, RNA molecule, DNA molecule, protein, proteoform, and/or any other molecule. Molecules can be naturally occurring molecules, modified molecules (e.g., molecules with one or more post-translational modifications), and/or any other molecule. Samples can be single-species samples (e.g., human samples, non-human samples, etc.), multi-species samples (e.g., for meta-proteomics studies), agriculture samples, wastewater samples, and/or any other sample types. The identity of the molecule of interest is preferably unknown, but can alternatively be known. S100 can optionally be iteratively performed. For example, S100 can be performed for each molecule of interest in one or more samples. The number of molecules of interest can be between 1-500,000 or any range or value therebetween (e.g., 1-1,000; 1-10,000; etc.), but can alternatively be greater than 500,000.

Experimental data can include proteomics data, metabolomics data, transcriptomics data, genomics data, epigenetics data, interactomics data, protein-protein interaction data, membrane permeability data, immunopeptideomics data, chemoproteomics data, metaproteomics data, any other molecular data, a combination thereof, and/or any other experimental data. Experimental data can be retrieved (e.g., from a database), received (e.g., from a user, from a third-party system, etc.), collected using an assay tool, simulated, predicted, predetermined, manually determined, a combination thereof, and/or otherwise determined. Examples of experimental data can include mass spectrometry data (e.g., spectra, intensities, mass/charge, retention times, ion mobility, etc.), other spectra, images, sequences (e.g., RNA and/or DNA sequences), intensities, mass, charge, ion mobility, signals, structure data, and/or any other data. Experimental data can be acquired using one or more assay tools and/or assay tool parameters. Experimental data can include experimental data of one or more data types. Examples of data types can include: spectra, types of spectra (e.g., DDA spectra, DIA spectra, TMT spectra, etc.), MS stage (e.g., MS1, MS2, etc.), sequences (e.g., short-read sequences), types of sequences (e.g., RNA, DNA, etc.), images, types of images, and/or any other data type.

In a first example, the experimental data includes one or more mass spectrometry spectra (e.g., MS1 and/or MS2 spectra) collected using DDA, DIA, and/or TMT modes. In a first specific example, the experimental data includes a single spectrum for a molecule of interest and/or spectra for molecules of interest with similar precursor masses and retention times. In a second specific example, the experimental data includes a mixed spectra for multiple molecules of interest in a sample. In a second example, the experimental data includes a sequence (e.g., short read sequence) for an RNA fragment and/or a DNA fragment.

Experimental data can be 1-dimensional, 2-dimensional, 3-dimensional, 4-dimensional, and/or have any other number of dimensions. The experimental data can optionally include a dataset with greater than a threshold number of dimensions (e.g., at least 2 dimensions, at least 3 dimensions, etc.). In a first example, experimental data can include a dataset that contains intensities (MS1 and/or MS2 intensities) across a single dimension: mass to charge ratio (m/z). In a second example, experimental data can include a dataset that contains intensities (MS1 and/or MS2 intensities) across two dimensions: m/z and retention time (e.g., the experimental data includes a 2D MS1/retention-time patch and/or a 2D MS2/retention-time patch). In a third example, experimental data can include a dataset that contains intensities (MS1 and/or MS2 intensities) across three dimensions: m/z, retention time, and ion mobility.

However, experimental data can be otherwise determined.

5.2. Determining Supplemental Information S150

The method can optionally include determining supplemental information S150, which can function to determine information associated with the experimental data and/or other information associated with the molecule of interest. S150 can be performed concurrently with S100, before S100, after S100, a combination thereof, and/or at any other time. Supplemental information can be retrieved, received, collected using an assay tool, simulated, predicted, predetermined, manually determined, determined using a model, a combination thereof, and/or otherwise determined. In a specific example, supplemental information can be received as metadata corresponding to the experimental data. Supplemental information can optionally be used as an input into a model (e.g., molecule identification model, scoring model, one or more encoder models, etc.).

Examples of supplemental information can include additional experimental data (e.g., collected using the same or a different assay tool type; collected using the same or a different assay tool mode; data for the molecule of interest or a different molecule; etc.), context parameters, predictions (e.g., predicted retention times, predicted spectra, predicted structure of peptides, predicted fragmentation sites in a precursor, predicted quantity of each fragment, predicted collision cross-sections of peptides in ion mobility spectrometry, etc.), physics information (e.g., physics of molecular fragmentation, molecular structures, etc.), and/or other information. Specific examples of additional experimental data include: measured retention times, nearby (e.g., adjacent) MS2 spectra (e.g., for molecules of similar mass), additional MS1 and/or MS2 spectra, precursor time of flight (e.g., ion mobility), precursor m/z, precursor intensity (e.g., peak intensity), peptide sequence length (e.g., precursor peptide length), sample pH and/or other sample environment features, molecular structure data, structural biology experimental data, imaging experimental data, batch identifier, sample location (e.g., in a well plate), and/or any other experimental data. Specific examples of context parameters can include: assay tool parameters (e.g., instrument type, make, model, manufacturer, data acquisition mode, instrument settings, MS stage, collision energy, etc.), data type, data dimensions (e.g., number of dimensions in the experimental data), fragmentation parameters (e.g., fragmentation method such as HCD fragmentation, CID fragmentation, etc.), digestion enzyme (e.g., trypsin, non-tryptic digestion, etc.), molecule modifications (e.g., biological modifications, TMT modifications, post-translational modifications (PTMs), any amino acid modification, etc.), molecule charge (e.g., charge state), molecule length, source protein functional annotation, mutation indicator, sample parameters (e.g., source organism of the sample such as human, plant, microorganism, etc.), and/or any other context for the experimental data. In a specific example, assay tool parameters can include type of mass spectrometry assay such as TOF-MS, LC-MS, GC-MS, CE-MS, IMS-MS, SIFT-MS, FT-MS, IT-MS, and/or any other mass spectrometry assay. In another specific example, assay tool parameters can include mass spectrometry data acquisition mode such as DDA, DIA, TMT, and/or any other mode. In a specific example, molecule modifications (e.g., such as PTMs) can include one or more of: cysteine carbamylation, methionine oxidation, deamidation, acetylation, phosphorylation, ubiquitination, glycosylation, and/or any other molecule modifications.

However, supplemental information can be otherwise determined.

5.3. Determining a Set of Candidate Molecules S200

The method can optionally include determining a set of candidate molecules S200, which can function to identify a subset of molecules that may be the molecule of interest (e.g., a subset of molecules that may match the experimental data). In a specific example, filtering the space of all molecules can enable more efficient identification of the molecule of interest.

The candidate molecules can be peptides, small molecules, RNA molecules, DNA molecules, and/or any other molecule. The candidate molecules can include unmodified molecules and/or modified molecules (e.g., modified peptides). Unmodified molecules can optionally be associated with one or more mass modifications (e.g., additional mass or reduced mass), where each mass modification corresponds to the change in mass (e.g., additional mass or reduced mass) of the unmodified molecule after a post-translational modification. The number of candidate molecules in the set of candidate molecules can be between 1-1 million or any range or value therebetween (e.g., at least 500; at least 1,000; at least 5,000; at least 10,000; at least 50,000; etc.), but can alternatively be greater than 1 million. The set of candidate molecules can optionally be specific to a molecule of interest (e.g., specific to one spectrum), general across multiple molecules (e.g., used for all spectra collected for a sample), and/or otherwise configured.

The set of candidate molecules can be manually determined, received (e.g., as a user input), determined based on the experimental data, determined based on supplemental information, retrieved (e.g., from a database), predetermined, randomly determined, determined using one or more models, a combination thereof, and/or otherwise determined. In a first example, candidate molecules can be selected that have similar mass and/or ion mobility to the molecule of interest (e.g., based on the experimental data). In a second example, the set of candidate molecules can be all or a subset of peptides for the source organism of the sample (e.g., all non-modified human peptides for a human sample). In a third example, the set of candidate molecules can be manually specified by a user. In a specific example, the set of candidate molecules can be an uploaded search database (e.g., a fasta file). In a fourth example, the set of candidate molecules can include modified molecules (e.g., molecules labeled with a labeling reagent for experimental data collected using TMT; peptides with post-translational modifications; etc.). In a fifth example, the set of candidate molecules can include mutated molecules (e.g., where the molecule of interest has been modified according to a mutation indicator). In a sixth example, a combination of filters can be used to select the set of candidate molecules (e.g., selecting a subset of source organism peptides based on mass).

Additionally or alternatively, the set of candidate molecules can be a subset of molecules determined using one or more search engines. In a specific example, a user can upload experimental data (e.g., a raw spectral file and a corresponding search database file); the spectral file and the corresponding search database can be passed through one or more first-generation search engines (e.g., as described in S400); the first-generation search results can then be used as the set of candidate molecules. The one or more first-generation search engines can optionally be run using a false discovery rate that is: at least at least 70%, 80%, at least 90%, at least 95%, and/or 100%.

However, the set of candidate molecules can be otherwise determined.

5.4. Processing Experimental Data S300

Processing experimental data S300 functions to: identify the molecule of interest (e.g., identifying and/or ranking peptide-spectrum matches), quantifying the molecule of interest, perform a similarity analysis across samples, map experimental data (e.g., sequences) to a reference, determine a quality of the experimental data (e.g., determine whether the experimental data acquisition should be repeated), and/or otherwise process the experimental data. S300 can be performed after S100, after S200, before downstream processing of the experimental data, before downstream experiments, and/or at any other time. S300 can optionally be iteratively performed. For example, S300 can be performed for each molecule of interest in a set of molecules (e.g., a set of molecules within a sample), for each sample in a set of samples, for each candidate molecule in a set of candidate molecules, a combination thereof, and/or otherwise iteratively performed. In an illustrative example, S300 can be iteratively performed to identify each molecule present in a sample (e.g., iteratively matching each spectrum in a set of spectra to a corresponding molecule prediction).

Processing experimental data can use one or more models, including a molecule identification model, a molecule encoder, an experimental data encoder, a sequence encoder (e.g., short sequence encoder, reference sequence encoder, etc.), a scoring model (e.g., a matching model), a clustering model, and/or any other model. In a specific example, the molecule identification model can include: an experimental data encoder, a molecule encoder, and a scoring model. In an illustrative example, the molecule identification model can function as a search engine to search a database of candidate molecules to identify one or more peptide-spectrum matches (PSMs) for an MS spectrum.

The models can include classical or traditional approaches, machine learning approaches, and/or be otherwise configured. The models can include regression (e.g., linear regression, non-linear regression, logistic regression, etc.), decision tree, clustering (e.g., k-means clustering, hierarchical clustering, etc.), association rules, dimensionality reduction (e.g., PCA, t-SNE, LDA, etc.), language processing techniques (e.g., LSA), neural networks (e.g., GNN, RNN, CNN, DNN, CAN, LSTM, RNN, FNN, encoders, decoders, deep learning models, transformers, etc.), ensemble methods (e.g., boosting, boostrapped aggregation, stacked generalization, gradient boosting machine method, random forest method, etc.), multimodal models, optimization methods, classification, rules, heuristics, equations (e.g., weighted equations, etc.), selection (e.g., from a library), lookups, regularization methods (e.g., ridge regression), Bayesian methods (e.g., Naiive Bayes, Markov, etc.), instance-based methods (e.g., nearest neighbor), kernel methods, support vectors (e.g., SVM, SVC, etc.), statistical methods (e.g., probability, multiple hypothesis testing, etc.), comparison methods (e.g., matching, distance metrics, thresholds, etc.), deterministics, genetic programs, foundation models (e.g., large language models), language models, vision-based models, and/or any other suitable model. The models can include (e.g., be constructed using) a set of input layers, output layers, and hidden layers (e.g., connected in series, such as in a feed forward network; connected with a feedback loop between the output and the input, such as in a recurrent neural network; etc.; wherein the layer weights and/or connections can be learned through training); a set of connected convolution layers (e.g., in a CNN); a set of fully connected layers; a set of self-attention layers; and/or have any other suitable architecture. Models can be trained, learned, fit, predetermined, and/or can be otherwise determined. Models can optionally be pretrained. In an example, models can be trained as described in S400.

Figure 2:
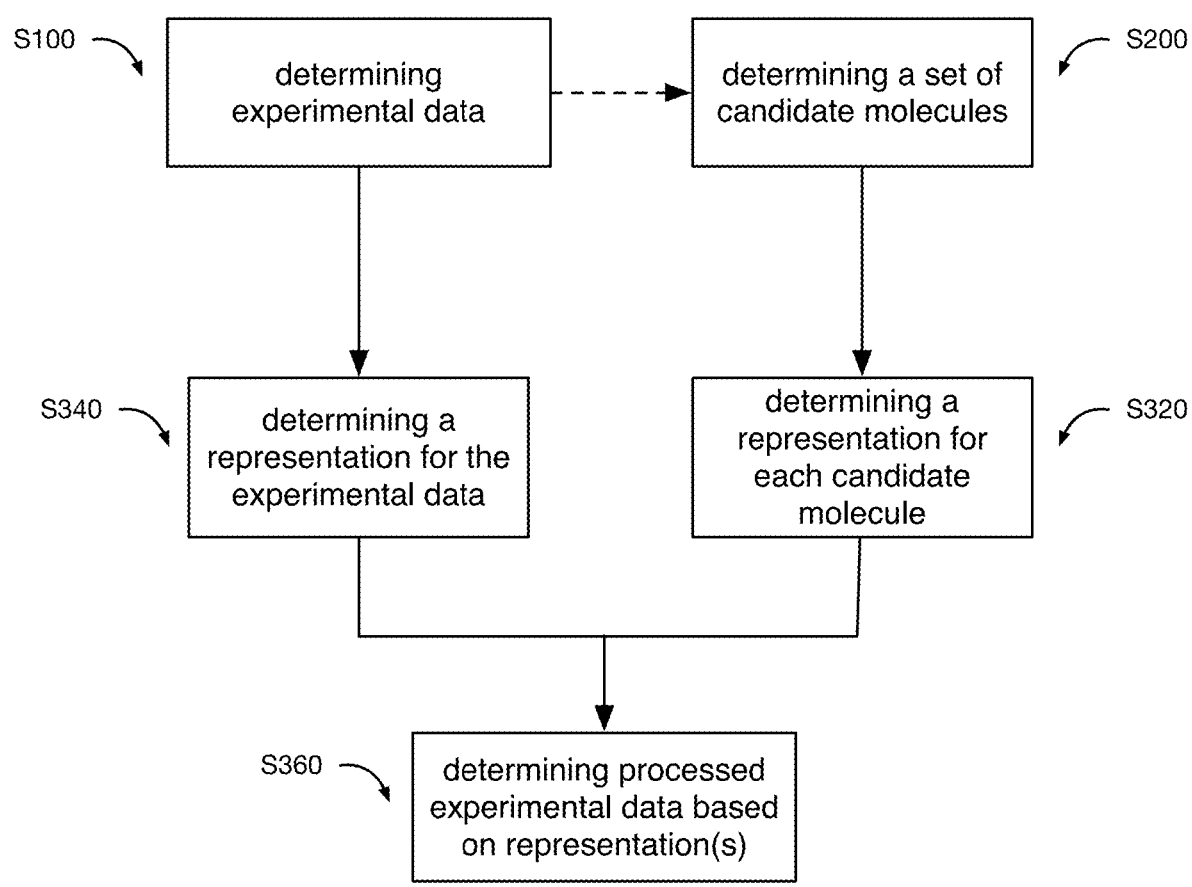
FIG. 2 is a schematic representation of an example of the method.

Processing experimental data preferably includes: optionally determining a representation for a candidate molecule S320 (e.g., for each candidate molecule in the set of candidate molecules), determining a representation for the experimental data S340, optionally include determining a representation for the supplementary information, and processing experimental data based on one or more representations S360. An example is shown in FIG. 2. Additionally or alternatively, experimental data can be processed without determining candidate molecule representations and/or experimental data representations.

Processing experimental data can optionally include determining a representation for a candidate molecule S320, which functions to encode information associated with the candidate molecule. S320 can be performed using a local system, a remote system, and/or a distributed system. S320 can optionally be performed for each candidate molecule in the set of candidate molecules. Representations for one or more candidate molecules can optionally be precomputed and stored in a database. The candidate molecule representation can be an embedding (e.g., an image, a vector, a matrix, etc.) and/or any other representation. The candidate molecule representation can optionally be determined using a molecule encoder. Inputs to the molecule encoder can include a molecule sequence (e.g., a peptide sequence for a candidate peptide), molecular structure (e.g., 3D structure of a small molecule and/or peptide), chemical formula, supplemental information, and/or any other information associated with the candidate molecule. Outputs from the molecule encoder can include the candidate molecule representation and/or any other suitable outputs. In specific examples, the molecule encoder can be or include one or more: GNNs (graph neural networks), RNNs, transformers, LLMs, geometric CNNs, any autoencoder, and/or any other model. In a specific example, the molecule encoder can include a language model, wherein inputs and/or training data can include evolutionary information (e.g., multiple different sequences across species that have the same shape and/or function). In another specific example, the molecule encoder can include a GNN, wherein inputs and/or training data can include the number of bonds separating atoms of interest in a molecule. In another specific example, the molecule encoder can include a geometric CNN, wherein inputs and/or training data can include the atoms of a molecule that are located within one or more shells (e.g., of predetermined radii). In another specific example, the molecule encoder can include a transformer and an RNN in parallel, wherein the embedding output by the transformer is combined with the embedding output by the RNN to generate the candidate molecule representation. However, candidate molecule representations can be otherwise determined.

Processing experimental data can optionally include determining a representation for the experimental data S340, which functions to encode the experimental data. S340 can be performed using a local system, a remote system, and/or a distributed system. In a first example, S340 can be performed locally, wherein the experimental data representation can be uploaded to a cloud system for processing (via S360). In a second example, S340 can be performed remotely. The experimental data representation can be an embedding (e.g., an image, a vector, a matrix, etc.) and/or any other representation. The experimental data representation can optionally be determined using an experimental data encoder. Inputs to the experimental data encoder can include the experimental data (e.g., a spectrum for a molecule of interest), supplemental information, and/or any other suitable inputs. Outputs from the experimental data encoder can include the experimental data representation and/or any other suitable outputs. In a specific example, for MS experimental data, the experimental data representation can preserve intensity information (e.g., associated with quantity of each fragment). In specific examples, the experimental data encoder can be or include one or more: vision-based models, RNNs, CNNs, GNNs, transformers, LLMs, any autoencoder, and/or any other model. In a specific example, the experimental data encoder can include a transformer and an CNN in parallel, wherein the embedding output by the transformer is combined with the embedding output by the CNN to generate the candidate molecule representation. In a first example, a first experimental data encoder can output experimental data representations for experimental data with a first number of dimensions (e.g., 1-dimensional MS spectra), and a second experimental data encoder can be output experimental data representations for experimental data with a second number of dimensions (e.g., 2-dimensional MS spectra). In a second example, the experimental data encoder can be configured to accommodate receiving as input experimental datasets with a variable number of dimensions (e.g., the same experimental data encoder can accommodate both a 1-dimensional MS spectral dataset or a 2-dimensional MS spectral dataset as the input). However, experimental data representations can be otherwise determined.

Processing experimental data can optionally include determining a representation for the supplementary information, which functions to encode the supplementary information. The supplementary information representation can be an embedding (e.g., an image, a vector, a matrix, etc.) and/or any other representation. The supplementary information representation can optionally be determined using an encoder. In a first example, the supplementary information can be encoded with the experimental data (e.g., in S340, via the experimental data encoder). In a second example, the supplementary information can be encoded in a separate encoder (e.g., a supplementary information encoder). However, experimental data representations can be otherwise determined.

Processing experimental data can optionally include processing experimental data based on one or more representations S360. In an example, S360 can be performed using a local system, a remote system, and/or a distributed system. For example, S360 can be performed remotely, using multiple cloud-based machines in parallel to compare the experimental data representation to each candidate molecule representation.

Figure 3:
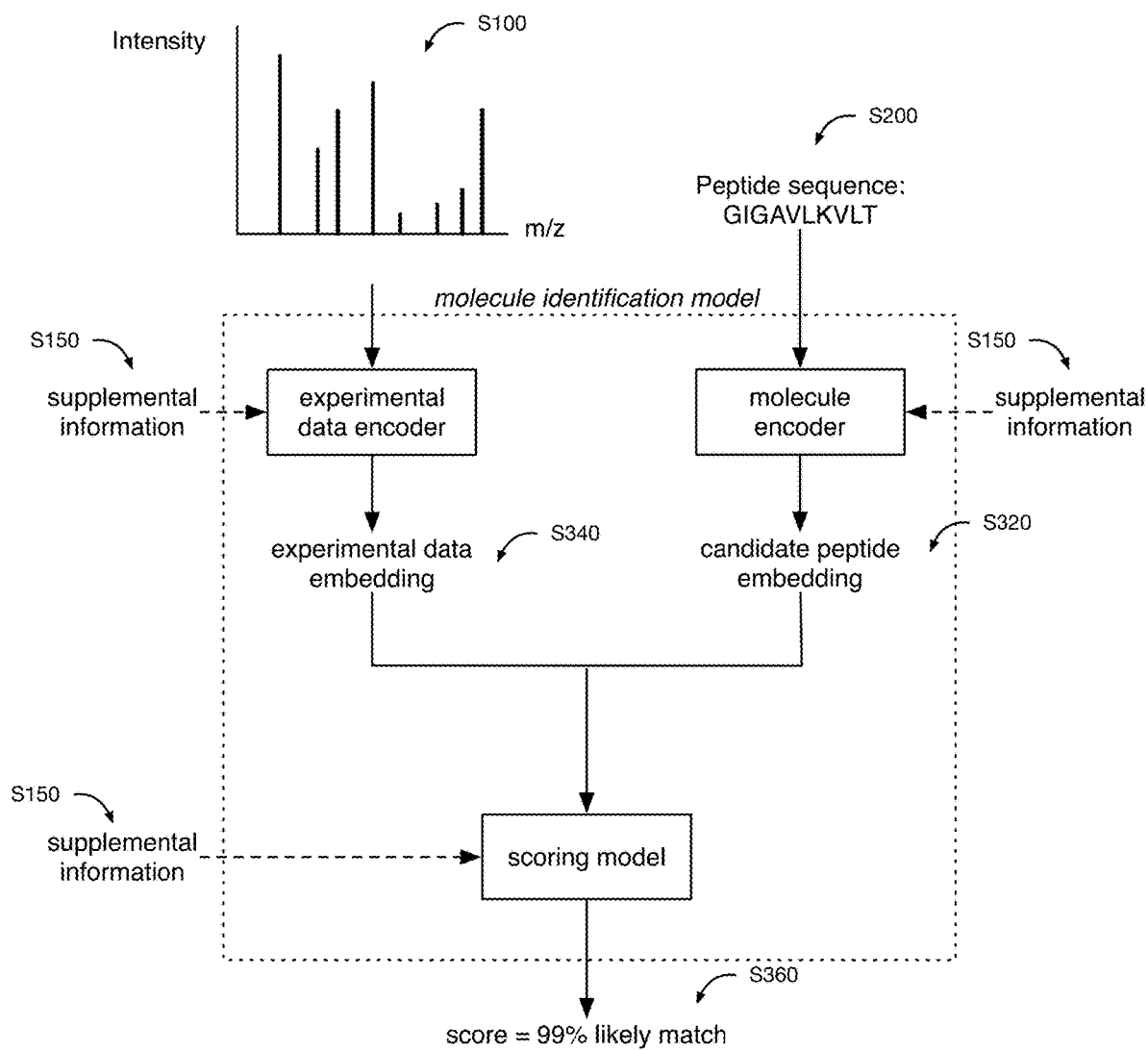
FIG. 3 is a schematic representation of an illustrative example of the method.

In a first variant, S360 can include identifying the molecule of interest. An example is shown in FIG. 3 and FIG. 11B. The molecule of interest is preferably identified without generating a predicted (theoretical) spectrum of a candidate peptide, but can alternatively be identified using a predicted spectrum (e.g., the candidate peptide representation can include a predicted spectrum and/or information associated with a predicted spectrum).

The molecule of interest can optionally be identified using a scoring model (e.g., matching model). Inputs to the scoring model can include: one or more candidate molecules, experimental data, supplemental information, a set of mass modifications (e.g., where each mass modification corresponds to the change in mass of an unmodified molecule after a post-translational modification), representations thereof, and/or any other suitable inputs. Experimental data and/or experimental data representations can optionally be labeled with supplemental information (e.g., data type). Outputs from the scoring model can include: a score for one or more candidate molecules, one or more candidate molecules (e.g., a selected candidate molecule), a score for one or more molecule modifications, one or more molecule modifications (e.g., one or more substituted amino acids, one or more added amino acids, one or more removed amino acids, etc.), a score (e.g., probability) for one or more molecule modification locations, one or more molecule modification locations, and/or any other suitable outputs. In examples the scoring model can include or use: concatenation, dot products, comparison methods (e.g., similarity metrics), statistical analysis (e.g., multiple comparison analysis), joint encoders, classification methods, image-based models (e.g., ResNet, Inception model, VGG, MobileNet, any image-based CNNs, etc.), cross-attention layers, ensemble methods, multimodal methods, and/or any other methods. In a first example, the scoring model can aggregate an experimental data representation and a candidate molecule representation (e.g., using concatenation, performing a dot product, etc.), and determine the score based on the aggregated representations (e.g., a concatenated vector, a synthetic image, etc.). In a second example, the scoring model can determine a similarity metric based on the experimental data representation and the candidate molecule representation, and determining the score based on the similarity metric. In a specific example, the score can be the similarity metric. In a specific example, the similarity metric can be a distance metric (e.g., a Euclidean distance between the experimental data representation and the candidate molecule representation in feature space).

The scoring model can optionally be an ensemble of scoring models. For example, each scoring model in the ensemble can be trained from a different set of initial parameter values (e.g., a randomized initial parameter values), using different training data (e.g., different subsets of training data), using different training methods, and/or otherwise configured. In a specific example, ensemble of scoring models can output an aggregated score (e.g., average score) from the individual scoring models in the ensemble.

The scoring model can optionally interface with one or more molecule encoders and/or experimental data encoders. For example, outputs from a molecule encoder (e.g., candidate molecule representation; S320) and an experimental data encoder (e.g., experimental data representation; S340) can be fed into the scoring model. In a specific example, the molecule identification model (e.g., an ensemble model) can include one or more molecule encoders, experimental data encoders, and the scoring model.

Figure 4:
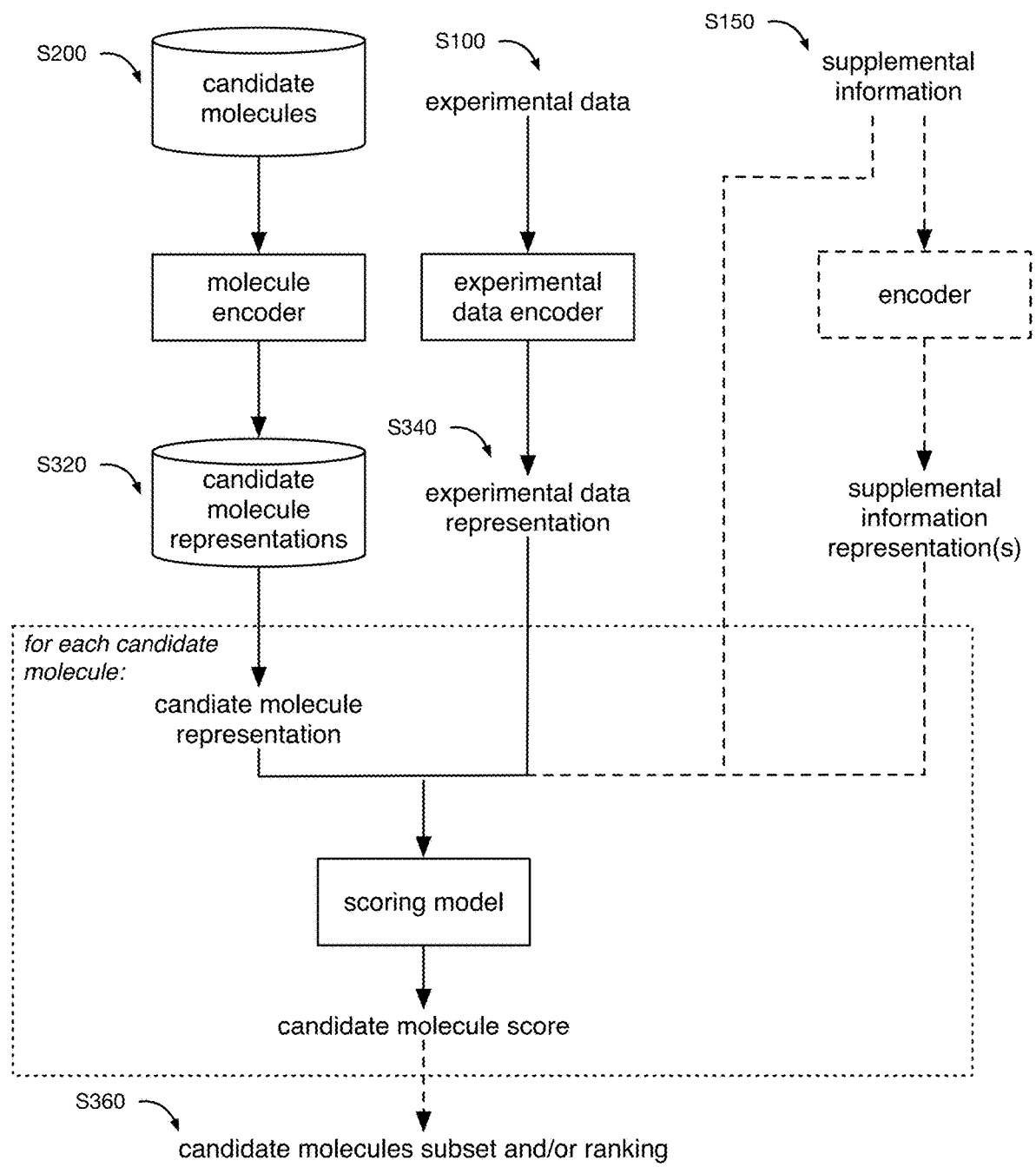
FIG. 4 is a schematic representation of a specific example of the method.
Figure 7:
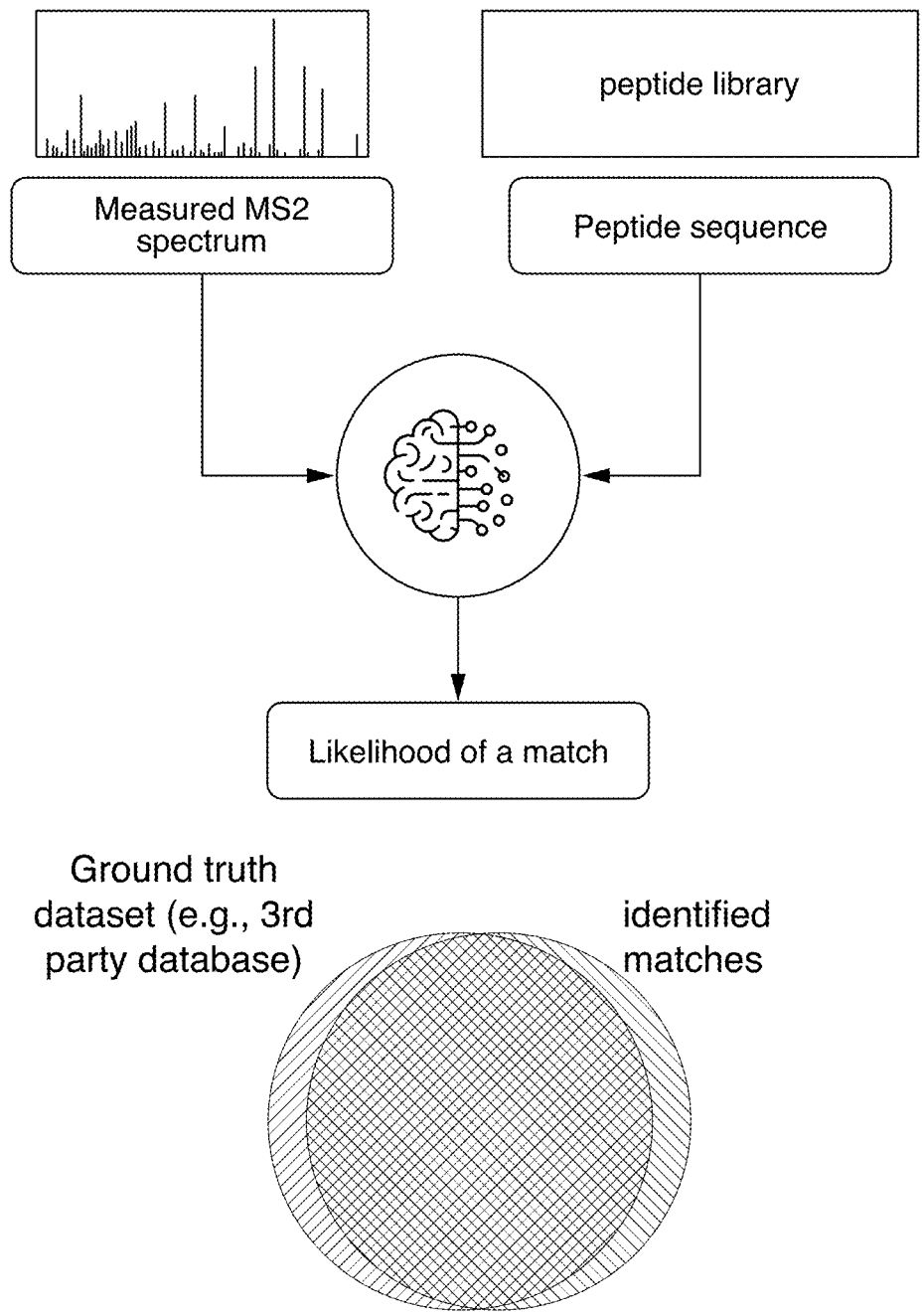
FIG. 7 depicts an illustrative example of the method.

The score can be qualitative, quantitative, relative, discrete, continuous, a classification, numeric, binary (e.g., match vs no match), and/or be otherwise characterized. The score can optionally be or include a confidence parameter. For example, the score can represent a probability that the molecule of interest (an unknown molecule identity) is a candidate molecule (a known molecule identity). An example is shown in FIG. 7. In an example, a score for each candidate molecule in the set of candidate molecules can be determined (e.g., iteratively using a scoring model, using multiple scoring model instances in parallel, etc.). An example is shown in FIG. 4. In a first specific example, the score for each candidate molecule in the set of candidate molecules can be provided to a user and/or otherwise used. In a second specific example, one or more candidate molecules can be selected from the set of candidate molecules based on the scores, wherein the subset of selected candidate molecules (and optionally the corresponding scores) can be provided to a user and/or otherwise used. In a first illustrative example, the highest scoring candidate molecule is selected (e.g., as the identified molecule of interest). In a second illustrative example, all candidate molecules with a score above a threshold are selected. Candidate molecules can optionally be ranked based on the scores.

However, the molecule of interest can be otherwise identified.

Figure 8A:
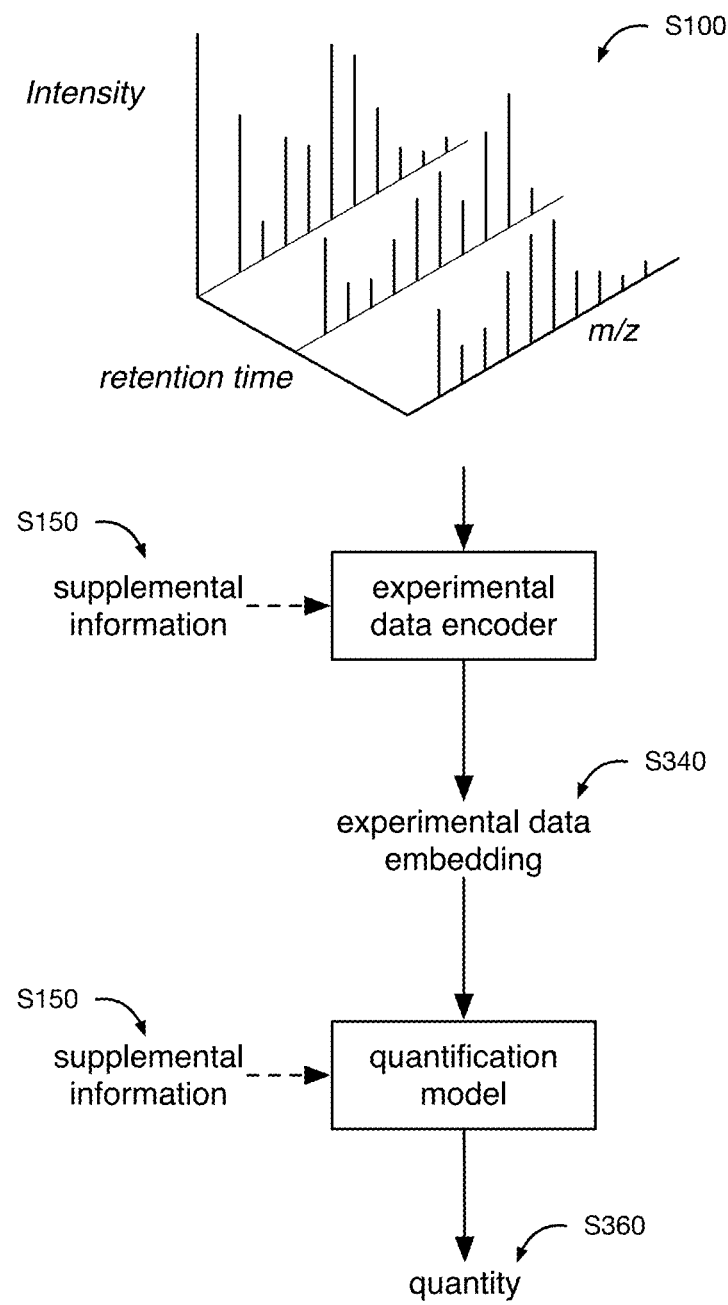
FIG. 8A depicts a first example of quantification.
Figure 8B:
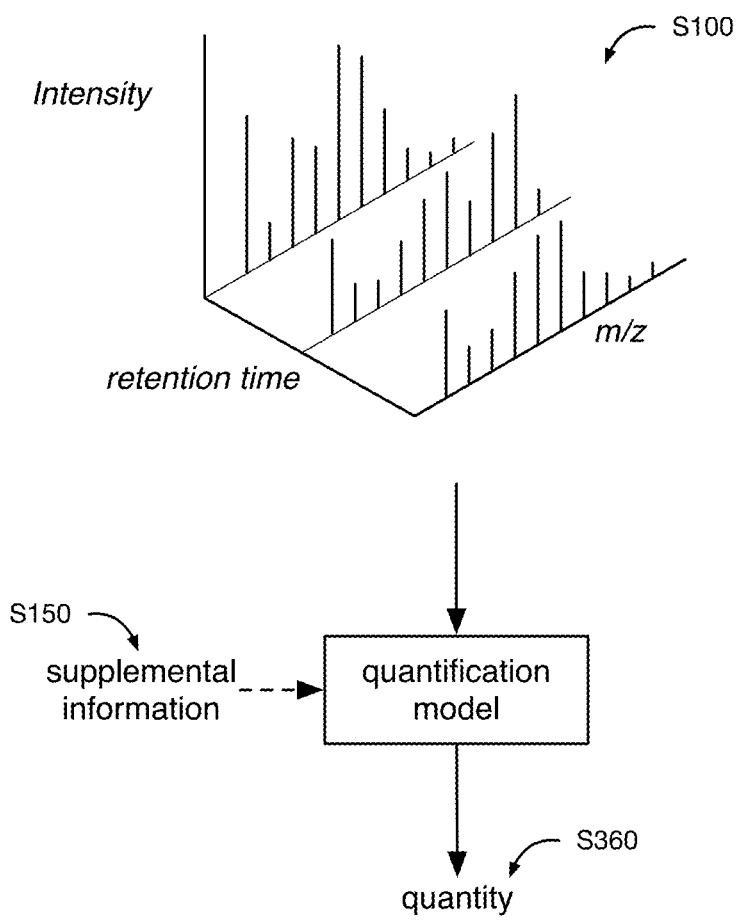
FIG. 8B depicts a second example of quantification.

In a second variant, S360 can include quantifying the molecule of interest. The molecule of interest can be quantified based on the experimental data, supplemental information, representations thereof, and/or any other information. In a first example, the molecule of interest can be quantified based on intensity information in a spectrum (e.g., an integral of intensity over retention time). In a second example, the molecule of interest can be quantified based on the experimental data and/or the experimental data representation using a quantification model (e.g., the scoring model as described in the first variant or a separate model). In a specific example, the experimental data representation can be the same representation used in the first variant or a different experimental data representation (e.g., determined using a separately trained experimental data encoder). Examples are shown in FIG. 8A and FIG. 8B. However, the molecule of interest can be otherwise quantified.

Figure 9A:
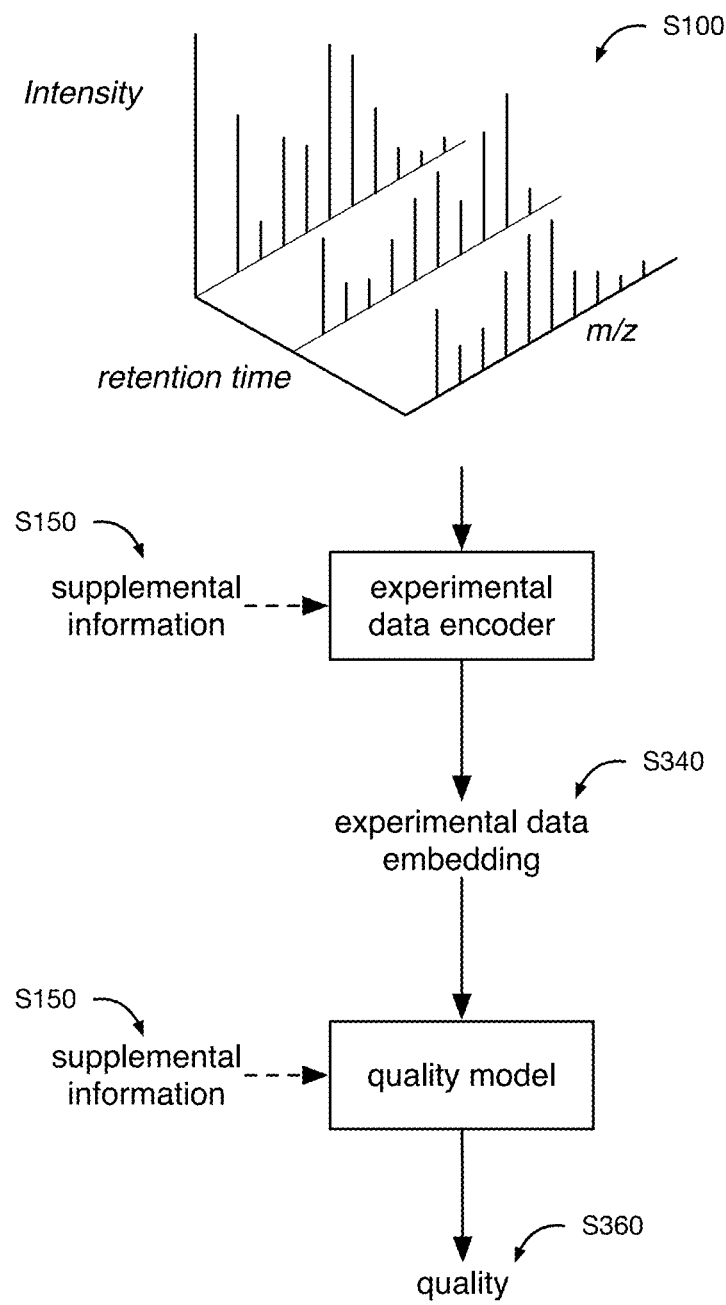
FIG. 9A depicts a first example of determining data quality.
Figure 9B:
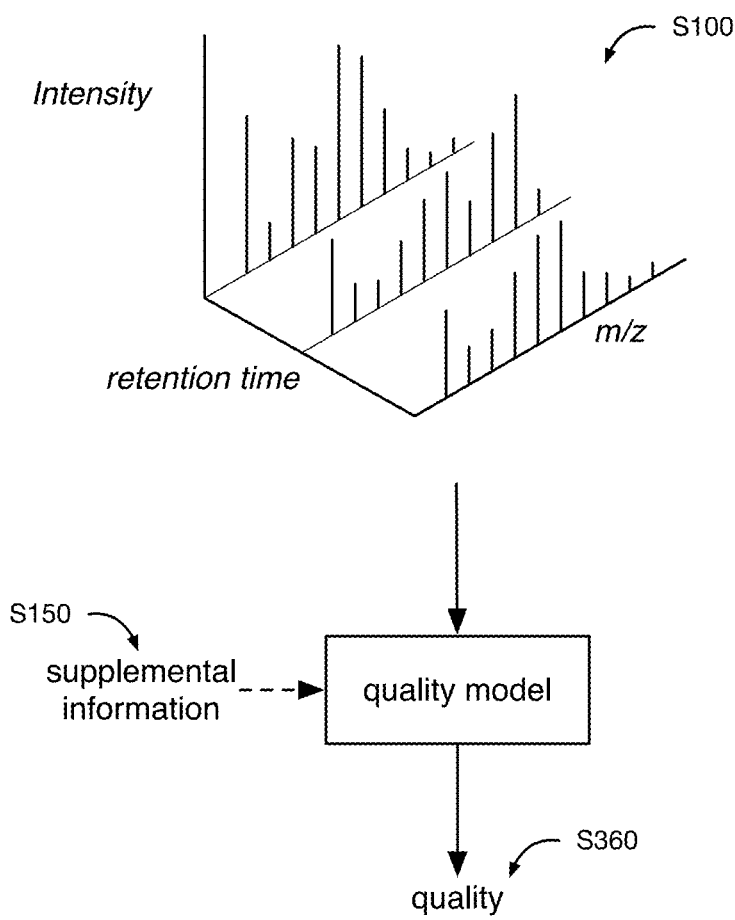
FIG. 9B depicts a second example of determining data quality.

In a third variant, S360 can include evaluating experimental data quality. The data quality can be evaluated based on the experimental data, supplemental information, the score for one or more candidate molecules (e.g., as determined via the first variant)), representations thereof, and/or any other information. In a first example, the data quality can be evaluated based on the experimental data and/or the experimental data representation using a data quality evaluation model. In a specific example, the experimental data representation can be the same representation used in the first variant or a different experimental data representation (e.g., determined using a separately trained experimental data encoder). Examples are shown in FIG. 9A and FIG. 9B. In a second example, data quality can be evaluated based on a similarity analysis between samples (e.g., as described in the fifth variant, below). However, the quality can be otherwise evaluated.

In a fourth variant, S360 can include identifying a post-translational modification and/or a location of the post-translational modification (e.g., modification location) in the identified molecule (e.g., the highest-scoring candidate molecule). In a specific example, S360 includes identifying a location (e.g., locus) of a post-translational modification in the sequence of the identified molecule. In an example, a scoring model (e.g., the same scoring model used in the first variant) can output an identified post-translational modification and/or the location of a post-translational modification within the identified molecule based on the experimental data representation, the representation for the identified molecule, and optionally a set of mass modifications. In a specific example, the scoring model can output a probability of a post-translational modification for each potential location (e.g., for each amino acid in the sequence). In a first example, the set of candidate molecules can include unmodified molecules and modified molecules (e.g., where each modified molecule is associated with a post-translational modification and corresponding modification location), wherein the scoring model outputs the identified modified molecule. In a second example, the set of candidate molecules can include unmodified molecules, and the scoring model can take as an additional input a set of mass modifications (e.g., within a user provided mass range), where each mass modification corresponds to the change in mass (e.g., additional mass or reduced mass) of an unmodified molecule after a post-translational modification. In this second example, an "open-window" search can optionally be performed, where the scoring model outputs an identified (unmodified) molecule as well as an identified post-translational modification and modification location.

In a fifth variant, S360 can include performing a similarity analysis between sets of experimental data.

Figure 10:
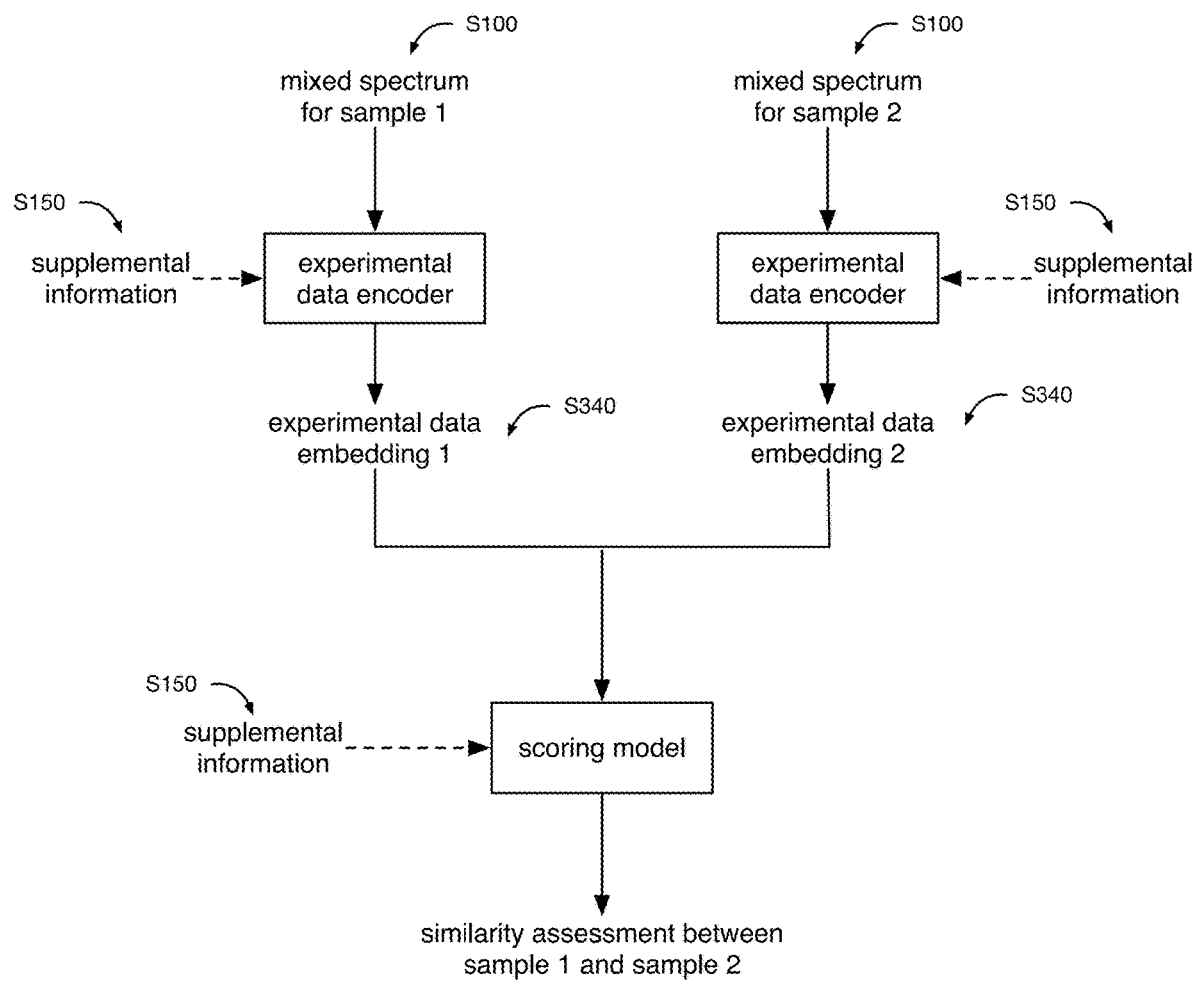
FIG. 10 is a schematic representation of an example of comparing samples.

In a first embodiment of the fifth variant, an experimental dataset (e.g., a mixed spectrum) can be determined for each sample in a set of samples; a representation can be determined for each experimental dataset (e.g., an embedding); and a similarity analysis can be performed based on the experimental data representations. An example is shown in FIG. 10. In variants example, this similarity analysis can be used for data quality evaluation (e.g., to identify outlier samples, to determine whether experimental data acquisition should be repeated, etc.). In a specific example, the similarity analysis can include a similarity metric (e.g., a distance metric).

Figure 6A:
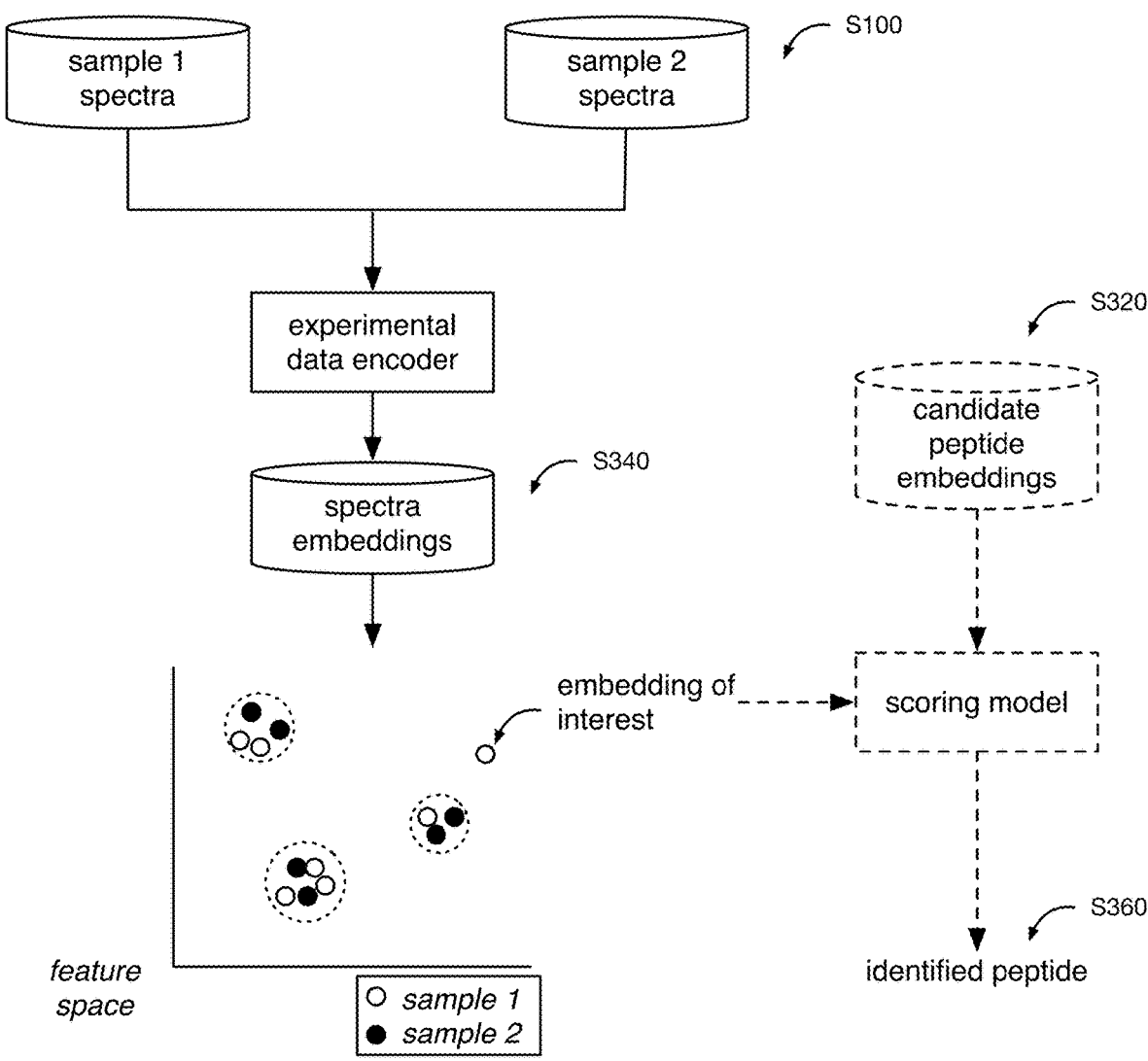
FIG. 6A is a schematic representation of a first specific example of the method, including similarity analysis.
Figure 6B:
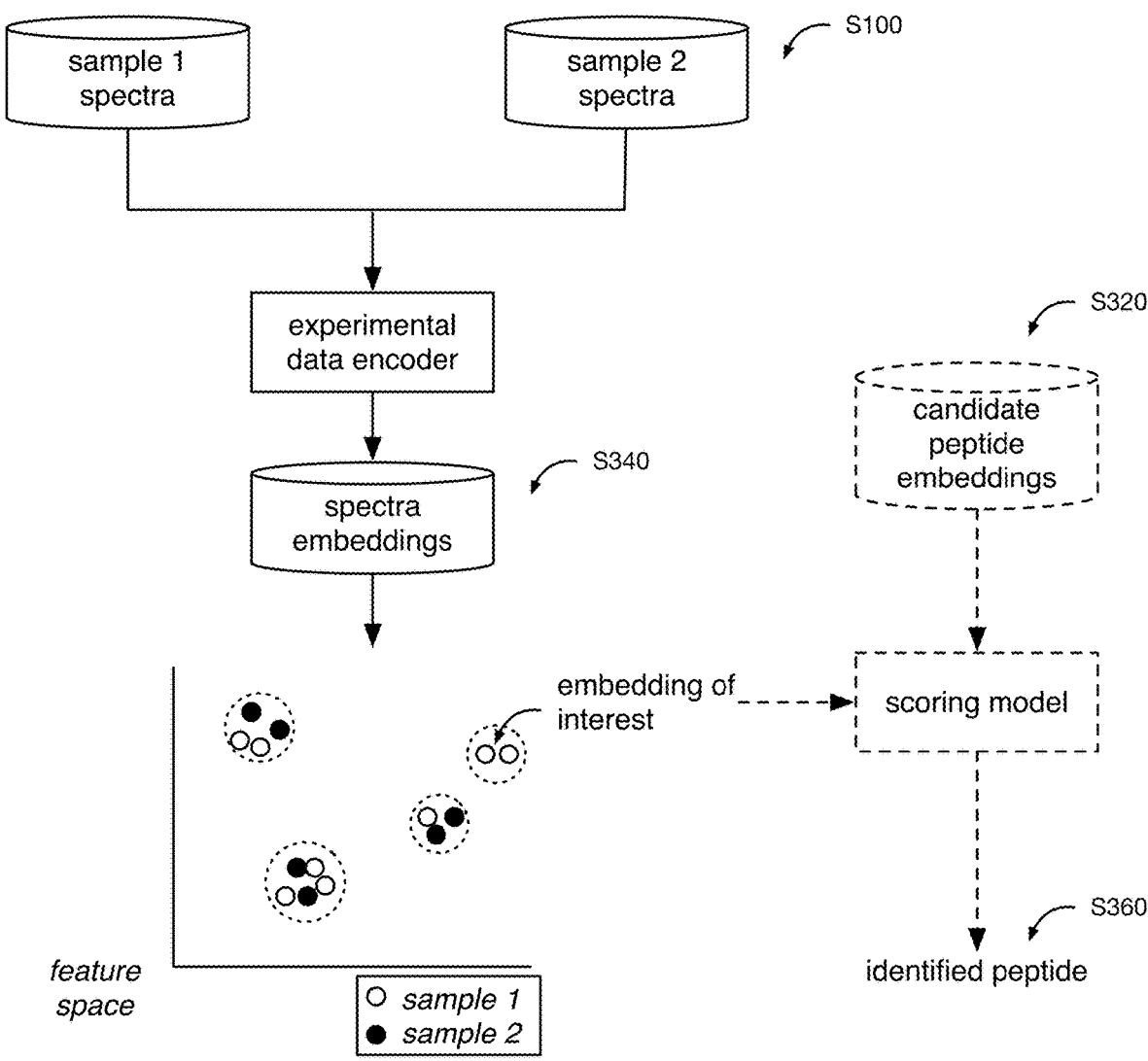
FIG. 6B is a schematic representation of a second specific example of the method, including similarity analysis.

In a second embodiment of the fifth variant, an experimental dataset (e.g., spectrum) can be determined for each molecule of all or a subset of molecules in a first sample and a second sample (e.g., S100); a representation can be determined for each experimental dataset (e.g., a spectrum embedding); and a similarity analysis can be performed based on the experimental data representations. In an example, the similarity analysis can include identifying an experimental data representation of interest (e.g., a spectrum embedding that likely corresponds to a molecule that is present in only one of the two samples). In a specific example, the samples can be samples of a multiple-arm experiment (e.g., one or more control samples and treated samples). The similarity analysis can use cluster analysis, statistical methods (e.g., outlier detection), comparison methods, and/or any other model or analyses. In a specific example, the experimental data representations (for both samples) can be clustered using a clustering model (e.g., each representation is assigned a cluster identifier), wherein similarity analysis can be performed based on the clusters. In specific examples, the representation of interest can be: an outlier (e.g., not clustered), clustered by itself, clustered with only representations from the same sample, and/or otherwise identified. The clustering feature space can be an embedding space (e.g., the embedding space used to encode the experimental data), a learned feature space, and/or any other feature space. The clustering model can be trained to learn: the clustering feature space, clustering threshold(s) (e.g., a threshold that impacts the number of clusters, the number of representations in each cluster, the purity of clusters, etc.), cluster purity, and/or any other cluster feature. In a specific example, the clustered experimental data representations can have between 50%-100% cluster purity (e.g., wherein a pure cluster contains only experimental data representations corresponding to a single molecule) or any range or value therebetween (e.g., at least 50%, at least 60%, at least 70%, at least 80%, at least 90%, etc.), but can alternatively have less than 50% cluster purity. Molecule(s) corresponding to one or more representations of interest can optionally be identified and/or quantified (e.g., as described in the first and/or second variants). Examples are shown in FIG. 6A and FIG. 6B. However, similarity analysis can be otherwise performed.

Additionally or alternatively, processing experimental data can include mapping experimental data (e.g., RNA short-read sequence, DNA short-read sequence, peptide sequences, etc.) to a reference (e.g., reference transcriptome, reference genome, protein sequence, etc.). In an illustrative example, processing experimental data can include identifying which proteins and/or genes are present in an experimental sample (e.g., protein expression) and/or quantifying protein and/or gene presence (e.g., a protein expression table). In an example, sequence(s) of interest can be mapped to candidate reference sequence(s) (e.g., gene sequences, protein sequences, etc.) to identify matching sequence(s) and/or a matching locus within a reference sequence. The sequence(s) of interest can optionally be sequences of molecules identified via S300.

For example, one or more (short) sequences of interest (e.g., peptide sequence, RNA/DNA short reads, etc) can be mapped onto one or more candidate reference sequences (e.g., protein sequences, gene sequences, etc.) using a scoring model. Inputs to the scoring model can include a (short) sequence of interest, one or more candidate reference sequences, supplemental information, representations thereof, and/or any other suitable inputs. Outputs from the scoring model can include a mapping score (e.g., probability and/or confidence score of a match between the sequence of interest and a candidate reference sequence), a locus (e.g., a locus of the short sequence of interest in a candidate reference sequence), one or more candidate reference sequences (e.g., one or more highest scoring candidate reference sequences, a ranking of candidate reference sequences, etc.), quantities (e.g., quantification of proteins and/or genes), and/or any other suitable outputs. For each candidate reference sequence, the number of (short) sequences of interest mapped to the candidate reference sequence, the mapping scores, and/or quantities (e.g., intensity of a peptide spectrum, abundance of DNA/RNA reads, etc.) can optionally be used to infer the protein and/or gene presence and/or abundance (e.g., using another model). The scoring model can be or include alignment models (e.g., Basic Local Alignment Search Tool (BLAST)), neural networks, and/or any other matching method. In a first example (e.g., an encoder-independent approach), the sequence of interest and candidate reference sequence(s) are directly used as inputs to the scoring model. In a second example (e.g., an encoder-based approach), a short sequence encoder can output a representation (e.g., embedding) for a sequence of interest, a reference sequence encoder can output a representation for a candidate reference sequence, and the sequence representations can be used as inputs to the scoring model. The short sequence encoder and the reference sequence encoder can be the same or different encoders. The reference sequence encoder can optionally be trained to take into account naturally occurring and/or synthetic sequence variations (e.g., using training data that includes sequence variations, using known sequence variants, using mutation probability analysis, etc.). In variants, the encoder-based approach can more accurately match sequences of interest that contain mutations, variants, and/or modifications.

However, experimental data can be otherwise mapped to a reference.

Processing experimental data can optionally include compressing experimental data. Processed and/or unprocessed experimental data can be compressed before S340 (e.g., compressed on a local computing system and transmitted to a remote computing system), during S340 (e.g., the experimental data representation is compressed experimental data), after S340 (e.g., compressing the experimental data representation), and/or at any other time. Compressing experimental data can use self-supervised compression methods (e.g., transformers; image-based compression methods; etc.), using a targeted removal of components of the experimental data, dimensionality reduction methods, and/or any other compression techniques. However, the experimental data can be otherwise compressed.

However, experimental data can be otherwise processed.

5.5. Training a Model S400

The method can optionally include training a model S400, which functions to train the molecule encoder, experimental data encoder, sequence encoder(s), scoring model, and/or any other model. S400 can be performed before S300, after S300 (e.g., using feedback after S300), and/or at any other time. S400 can additionally or alternatively include model validation and/or evaluation (e.g., using benchmark and/or performance metrics). In specific examples, the model(s) can be trained to prevent or reduce overfitting and/or hallucination. Models can be trained or learned using: supervised learning, unsupervised learning, self-supervised learning, semi-supervised learning, weakly-supervised learning, multiple-instance learning, reinforcement learning, transfer learning, fitting, interpolation, approximation, backpropagation, and/or otherwise trained. Models can be learned or trained on: labeled data (e.g., data labeled with the target label), unlabeled data, positive training sets, negative training sets, and/or any other suitable set of data. Training data can be measured, retrieved from a database (e.g., third-party database; a synthetic library; etc.), augmented (e.g., with artificial noise), simulated, manually determined, randomly determined, and/or otherwise determined. Training data can optionally include data for complex samples (e.g., cell, tissue, etc.; with unknown protein content), simple samples (e.g., synthetic peptides with known sequences), multiple species, a single species, a combination thereof, and/or any other data. Training data can optionally include data for multiple: data types, numbers of experimental data dimensions, digestion enzymes, collision energies, fragmentation methods, a combination thereof, and/or any other supplemental information classifications.

Models can be trained individually, together (e.g., an ensemble molecule identification model trained using end to end learning), a combination thereof, and/or otherwise trained. For example, encoders (e.g., the molecule encoder and the experimental data encoder; the short sequence encoder and the reference sequence encoder; etc.) and the scoring model can collectively form an ensemble model (the molecule identification model), wherein each submodel can be individually trained (e.g., updated) and/or trained together (using end-to-end learning). In a specific example, a molecule encoder for small molecules and/or modified peptides (e.g., PTM peptides) could be partially or fully pretrained (e.g., to accommodate the large search space of small molecules and/or modified peptides); the molecule encoder can then optionally be updated using end-to-end learning. In an example, the molecule encoder can be (individually) trained using one or more objectives. In examples, objectives can include molecule parameters, such as: molecule sequence, molecule function, molecule localization, molecule structure, experimental data (e.g., measurements of the molecule such as an MS spectrum), physical chemical properties, and/or any other molecule parameter. In a first specific example, the molecule encoder can output a training representation for a training molecule, a decoder can decode the training representation to predict a molecule parameter (e.g., predicted experimental data, predicted sequence, etc.), and the predicted molecule parameter can be compared to a known molecule parameter (e.g., known experimental data, known sequence, etc.). In a second specific example, a molecule encoder that includes a language model can be trained using mask token training.

Models can optionally be trained to be specific or general to supplemental information (e.g., molecule lengths, molecule charges, molecule modifications, digestion enzymes, instrument settings, data types, species, etc.). For example, an individual model can be trained for different values of supplemental information and/or multiple models can be trained for different values of supplemental information. In a first specific example, a scoring model can accept different experimental data representations corresponding to different values of supplemental information (e.g., different data types, different numbers of experimental data dimensions, etc.). In a second specific example, an ensemble model can include multiple experimental data encoders pretrained for different values of supplemental information (e.g., different data types, different numbers of experimental data dimensions, etc.) and connected using logic. Models can optionally be trained for a first supplemental information value (e.g., DDA), then retrained (e.g., fine tuned, updated, etc.) for a second supplemental information value (e.g., DIA). In an illustrative example, the molecule encoder can be the same for different data types (e.g., DDA and DIA spectra), while the experimental data encoder can be retrained for different data types.

Models can optionally be modular (e.g., an encoder can be replaced with another encoder). In a first illustrative example, a first molecule encoder that is trained using a first data type (e.g., peptide sequences) can be replaced with a second molecule encoder that is trained using a second data type (e.g., molecular structures). In a second illustrative example, a first experimental data encoder that is trained using a first data type (e.g., DDA) can be replaced with a second experimental data encoder that is trained using a second data type (e.g., DIA).

Figure 5A:
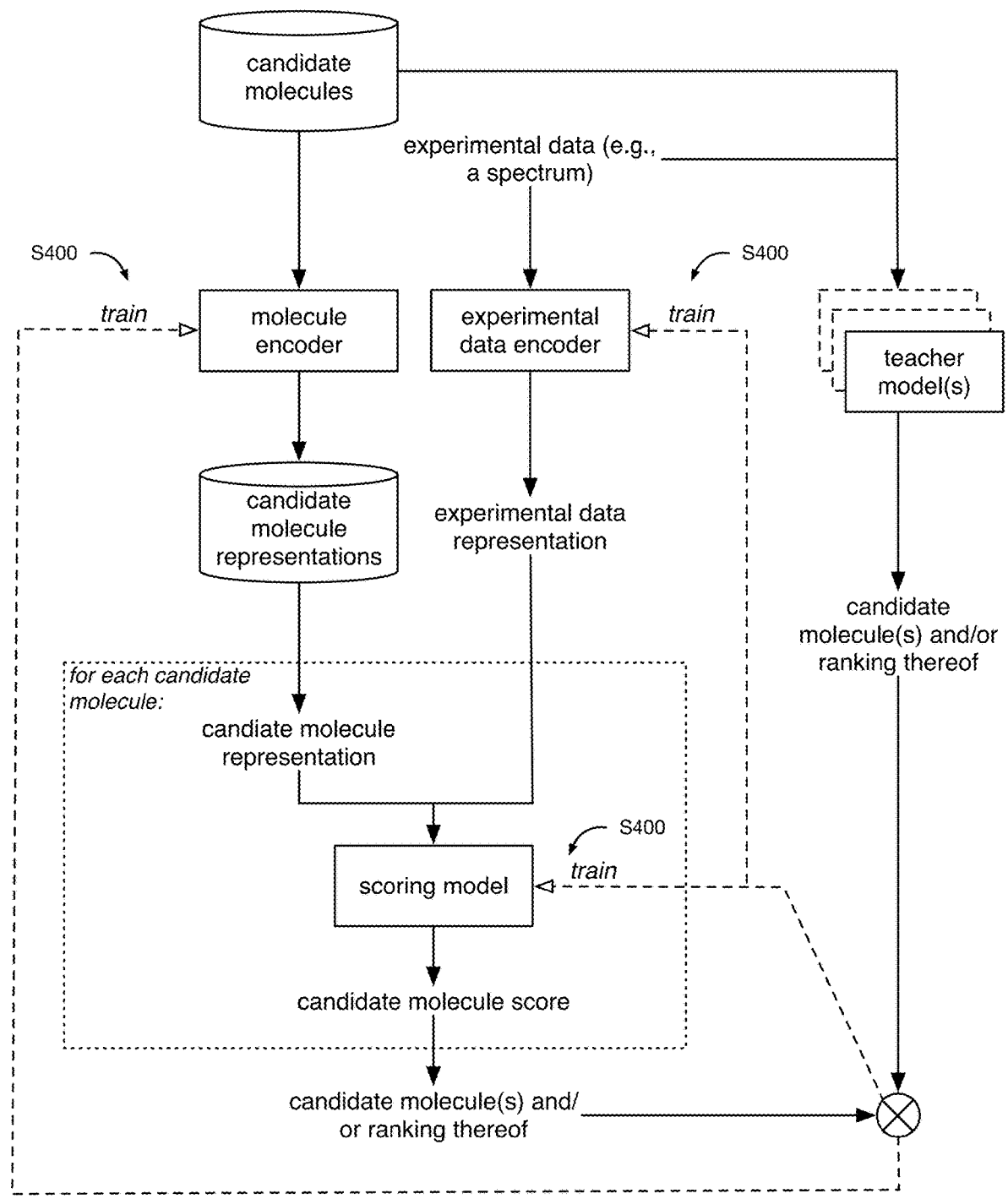
FIG. 5A-5C are schematic representations of examples of model training.

In a first variant, a model can be trained and/or evaluated using one or more teacher models. An example is shown in FIG. 5A. In a first embodiment of the first variant, the teacher model can be a preexisting preprocessing model (e.g., a preexisting existing PSM search engine). In a specific example, preexisting preprocessing models can include first-generation search engines and/or second-generation search engines. As used herein, first-generation search engines can refer to PSM search engines that rely on a hand-crafted heuristic for scoring matches between fragment ion spectra to peptide sequences. Specific examples of first-generation search engines include Comet, MaxQuant, MSFragger, MS-GF$^+$, Sage, and/or Sequest. In a specific example, first-generation search engines do not take the intensities of fragment ions into account. As used herein, second-generation search engines can refer to PSM search engines that use deep learning models trained using decoys (e.g., an example is shown in FIG. 11A). Specific examples of second-generation search engines and/or methods that utilize second-generation search engines can include: Prosit, Fragpipe, Percolator, and/or PeptideProphet. In a second embodiment of the first variant, the teacher model can be a pretrained scoring model (e.g., a scoring model trained using a preexisting preprocessing model as a teacher model). In a specific example the scoring model can be iteratively trained using a previous iteration as the teacher model.

The loss can be calculated by comparing one or more molecule predictions (e.g., highest scoring molecule(s)), molecule rankings, and/or molecule scores output by the scoring model to one or more identified molecules, ranked molecules, and/or molecule scores output by the one or more teacher models. In a first embodiment, the loss used to train the model(s) can be determined using a single teacher model. In a first example, the loss can be calculated by comparing the molecule prediction determined using the scoring model (e.g., the highest-scoring candidate molecule) to the molecule identified using a single teacher model. In a specific example, the candidate molecule ranked first (e.g., as a match to the experimental data) by the teacher model can be labeled with a positive label, and one or more subsequent candidate molecules (e.g., ranked as lower likelihood matches such as second ranked, third ranked, etc.) can be labeled with a negative label. In a second example, multiple top candidate molecules as ranked by the teacher model can be used to calculate a ranking-based loss. In a second embodiment, the loss used to train the model(s) can be determined using multiple (different) teacher models (e.g., at least 2, at least 3, etc.). In an example, the loss can be a combined loss, calculated by combining (e.g., averaging) the loss determined using a first teacher model (e.g., as in the first example) with a loss determined using a second teacher model. In a specific example, the loss can be determined based on molecule predictions determined using at least two (different) first-generation search engines.

In a second variant, a model can be trained and/or evaluated using training data including known matches between experimental data and molecules (labeled with a positive training target) and decoy matches between experimental data and decoy molecules (e.g., shuffled peptide sequences; labeled with a negative training target).

In a third variant, a model can be trained and/or evaluated using training data that includes a known match between experimental data and one or more molecules. In a specific example, the training data can include ground-truth experiments (e.g., using synthesized peptides).

Figure 5B:
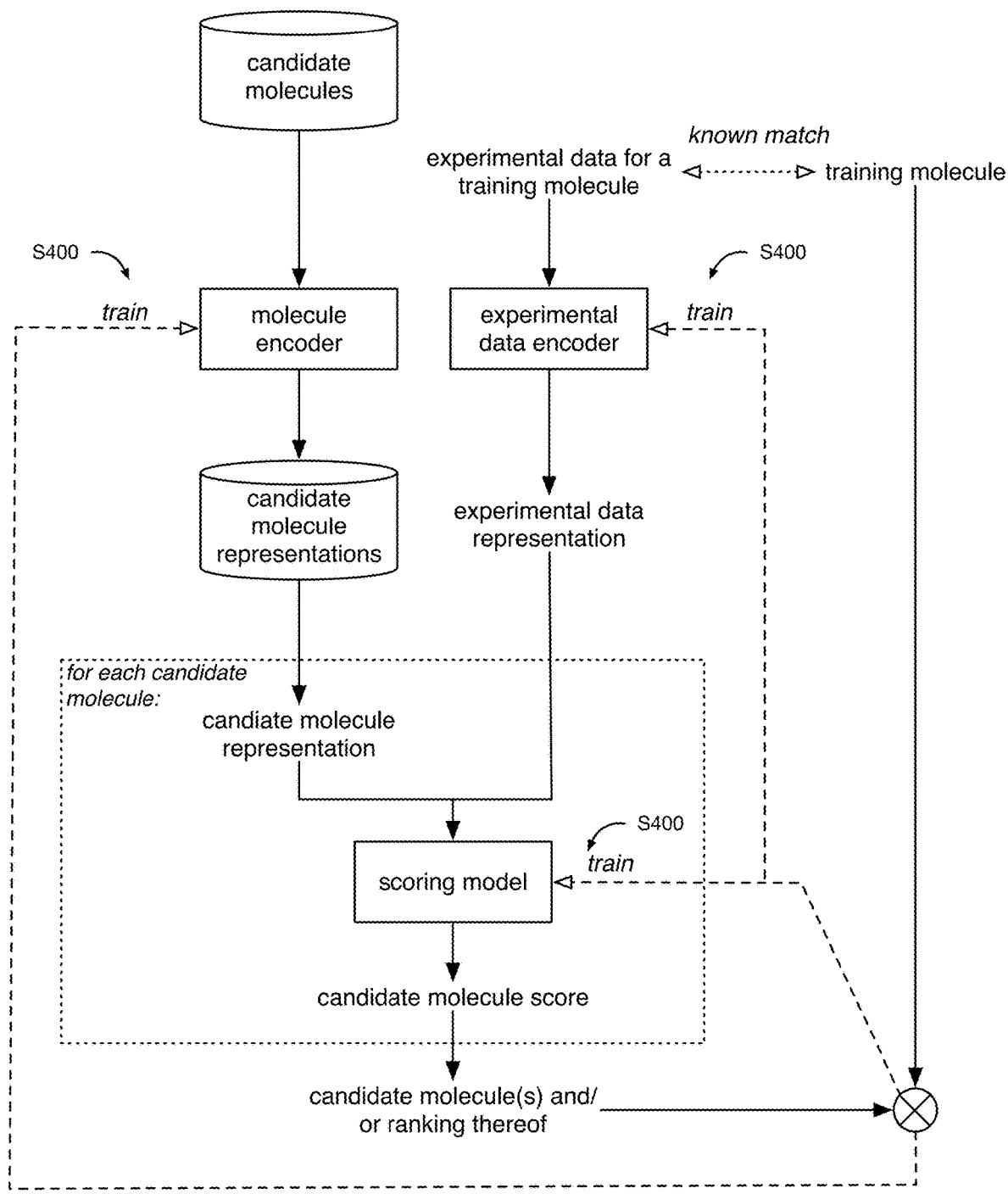
Figure 5C:
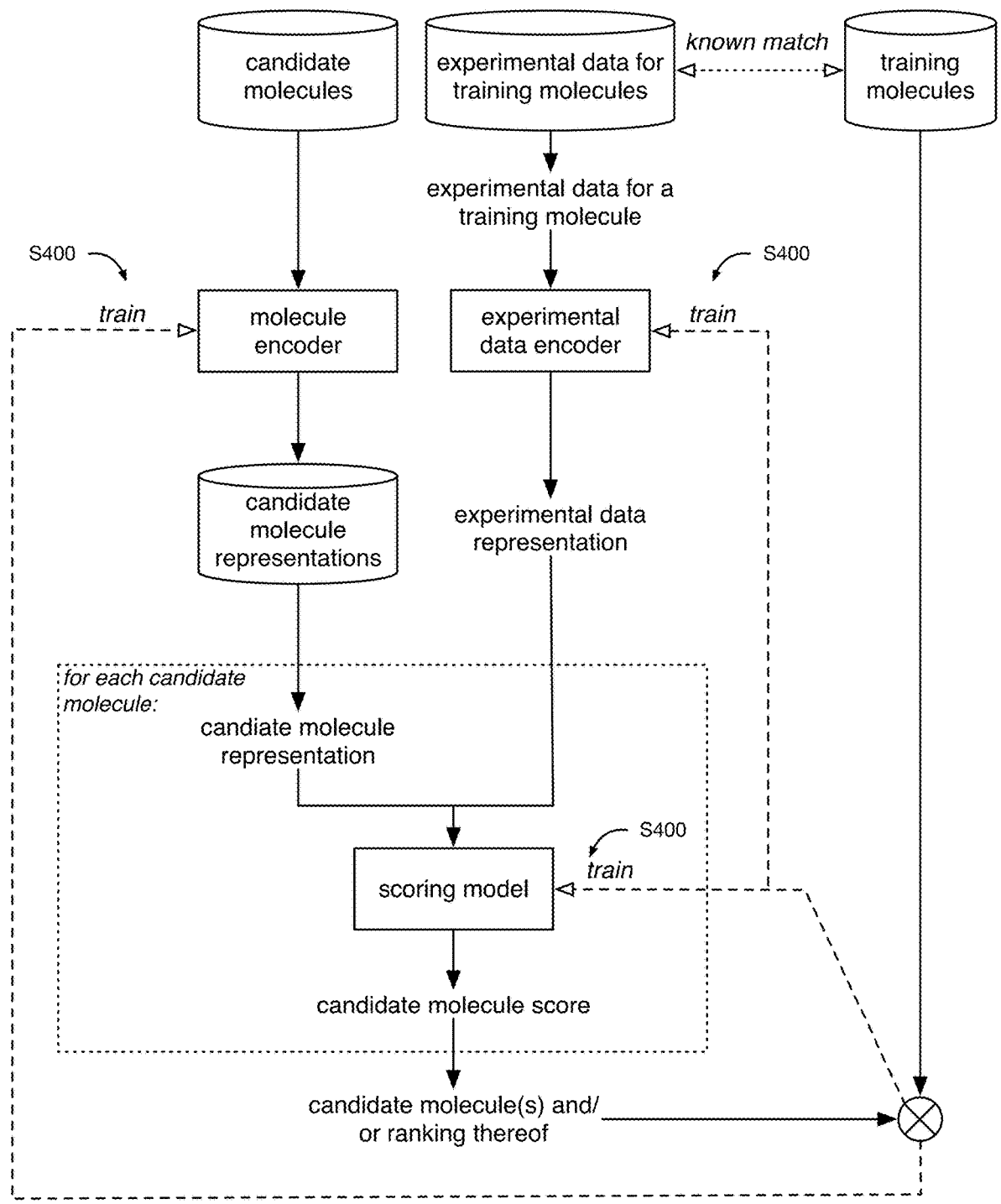

In a first embodiment of the third variant, a known match between an individual molecule and a spectrum can be used to train the model. An example is shown in FIG. 5B. In a specific example, the loss used to train the model(s) can be calculated by comparing the molecule prediction for a spectrum of interest (e.g., determined using the molecule identification model) to the known molecule match for the spectrum of interest. In a second embodiment of the third variant, a known match between a set of molecules (e.g., a "bag" of molecules) and a set of spectra (e.g., a "bag" of spectra") can be used to train the model. An example is shown in FIG. 5C. For example, the training data can include a database of experimental data (e.g., MS spectra) for a sample of known molecules, without individual mappings between each molecule in the sample and a corresponding spectrum. In an example, the loss used to train the model(s) can be calculated by comparing the molecule prediction for a spectrum of interest (e.g., determined using the molecule identification model) to the known the set of molecules corresponding to the spectrum of interest. In an example, the molecule identification model and/or models therein (e.g., the molecule encoder, the experimental data encoder, etc.) can be trained by determining a loss for a set of molecule predictions (e.g., predicted using the molecule identification model) determined for a set of training spectra (e.g., the set of spectra collected for a training sample). In this example, the loss can be determined based on a known match between a training sample and the set of training spectra, the training sample containing a set of training molecules. In a specific example, the loss can be determined based on a comparison between the set of molecule predictions and the set of training molecules, wherein individual matches between each (individual) training spectrum in the set of training spectra and a corresponding (individual) training molecule in the set of training molecules is not known (e.g., 1:1 matches between spectra and molecules are not known). In an example, the loss can be or be determined based on: an accuracy metric, a sensitivity metric, a specificity metric, an F1 score, and/or a combination thereof. In a specific example, for a set of training spectra, the training molecules corresponding to that set of training spectra are known (and the training molecules that do not correspond to that set of training spectra are also known); the loss can be an accuracy metric determined based on the number of true-positive and true-negative molecule(s) predicted based on the set of training spectra (e.g., predicted using the molecule identification model), determined based on a comparison between the molecule predictions and the training molecules. In a specific example, the accuracy metric can be a fraction between the number of true-positive molecules predicted and the number of true-negative molecules predicted. In a third embodiment of the third variant, a combination of the previous examples can be used.

In a fourth variant, a model can be trained (e.g., updated) and/or evaluated using feedback from validation experiments (e.g., the identified candidate molecule was correct or incorrect). In a specific example, a model can be fine-tuned (e.g., fine-tuning weights) using data for an individual assay tool (e.g., specific to a lab).

In a fifth variant, a combination of the previous variants can be used. In a first example, a model can be evaluated (e.g., to measure model generalization to new peptides; to ensure the model is learning spectra features; etc.) using synthetic libraries, decoy-based evaluation, organism-based cross-validation studies, and/or model interpretation (e.g., explainability). In a second example, for a given spectrum of interest, if there is a known molecule match (e.g., as determined by a biological, non-synthetic experimental dataset), the loss is calculated using that known molecule match (e.g., as described in the third variant). If there is not a known molecule match, pass the spectrum of interest through one or more teacher models (e.g., first-generation search engines). If the teacher model(s) identify a molecule match (e.g., with greater than a threshold score), the loss can be calculated based on the match(es) from the teacher model(s) (e.g., as described in the first variant) and/or a match to a set of multiple molecules (e.g., as described in the third variant). If the teacher model(s) do not identify a molecule match (e.g., with greater than a threshold score), the loss can be calculated based on a match to a set of multiple molecules (e.g., as described in the third variant).

Models are preferably not trained using decoys (e.g., training data that includes decoys), but can alternatively be trained using decoys. Models are preferably not trained using Percolator and/or other second-generation search engines that are trained using decoys, but can alternatively be trained using Percolator.

Figure 15:
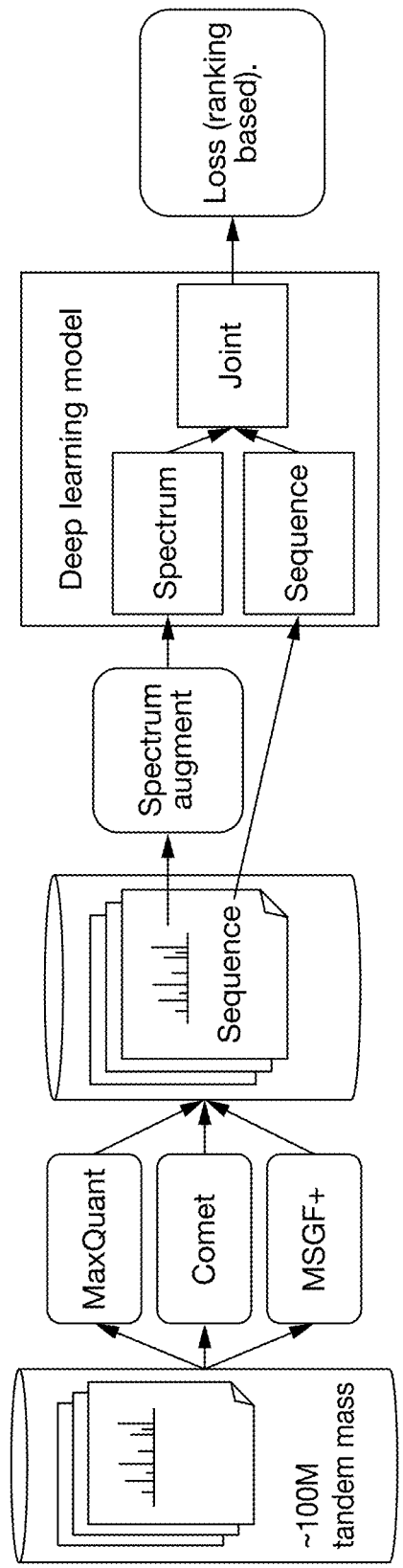
FIG. 15 depicts a schematic representation of an example model training framework, including: searching publicly-available datasets containing training spectra using three search engines (e.g., MaxQuant, Comet and MSGF+.) to output matches between the training spectra and identified peptides, ranking the identified peptides, augmenting the training spectra with artificial noise, passing the augmented training spectra through the molecule identification model, and training the molecule identification model to rank the top peptides (e.g., the top 3 peptides) identified by each search engine.

In an illustrative example, first, a training dataset of tandem mass spectra and, for each spectrum, a ranked list of (possibly modified) candidate peptide sequences can be identified by searching one or more databases with one or more different first-generation search engines (e.g., where the ranked list of candidate peptide sequences includes any peptide sequence identified by at least one first-generation search engine). Each raw spectrum can optionally be centroided. Each raw spectrum can optionally be augmented (e.g., with additional noise). For each (spectrum, sequence) pair, the molecule identification model can predict a single score, and a corresponding predicted ranking can be determined. A ranking loss can then be used for backpropagation. An example is shown in FIG. 15.

However, models can be otherwise trained.

6. Specific Examples

A numbered list of specific examples of the technology described herein are provided below. A person of skill in the art will recognize that the scope of the technology is not limited to and/or by these specific examples.

Specific Example 1. A method for molecule identification, comprising: determining a mass spectrometry spectrum for a molecule; determining an embedding for the mass spectrometry spectrum, using a first encoder; for each candidate molecule in a set of candidate molecules: determining an embedding for the candidate molecule based on a sequence for the candidate molecule, using a second encoder; and using a scoring model, determining a score for the candidate molecule based on the embedding for the mass spectrometry spectrum and the embedding for the candidate molecule; and selecting a candidate molecule from the set of candidate molecules based on the scores.

Specific Example 2. The method of Specific Example 1, wherein determining the score for the candidate molecule comprises: determining a similarity metric based on the embedding for the mass spectrometry spectrum and the embedding for the candidate molecule; and determining the score based on the similarity metric.

Specific Example 3. The method of Specific Example 2, wherein the similarity metric comprises a distance between the embedding for the mass spectrometry spectrum and the embedding for the candidate molecule.

Specific Example 4. The method of any of Specific Examples 1-3, wherein the first encoder comprises a CNN.

Specific Example 5. The method of any of Specific Examples 1-4, wherein the first encoder further comprises a transformer.

Specific Example 6. The method of any of Specific Examples 1-5, wherein the second encoder comprises a combination of an RNN and a transformer.

Specific Example 7. The method of any of Specific Examples 1-6, wherein the mass spectrometry spectrum comprises an experimental dataset containing intensities across at least two dimensions, wherein a first dimension of the experimental dataset is mass to charge ratio (m/z) and a second dimension of the experimental dataset is retention time.

Specific Example 8. The method of Specific Example 7, wherein the experimental dataset contains intensities across a third dimension, wherein the third dimension is ion mobility.

Specific Example 9. The method of any of Specific Examples 1-8, wherein the first encoder is configured to accommodate receiving as input experimental datasets with a variable number of dimensions.

Specific Example 10. The method of any of Specific Examples 1-9, further comprising determining a location of a post-translational modification within the candidate molecule based on the embedding for the mass spectrometry spectrum and the embedding for the candidate molecule.

Specific Example 11. The method of any of Specific Examples 1-10, wherein the first encoder is trained by determining a loss for a set of molecule predictions corresponding to a set of training spectra, wherein the loss is determined based on a known match between a training sample and the set of training spectra, the training sample comprising a set of training molecules, wherein individual matches between each training spectrum in the set of training spectra and a corresponding training molecule in the set of training molecules is not known, wherein the set of molecule predictions is determined using the first encoder, the second encoder, and the scoring model.

Specific Example 12. The method of Specific Example 11, wherein the loss for the set of molecule predictions is further determined based on a second set of molecule predictions determined using at least two first-generation search engines.

Specific Example 13. The method of any of Specific Examples 11-12, wherein the loss comprises an accuracy metric determined based on a number of true-positive molecule predictions and a number of true-negative molecule predictions, the number of true-positive molecule predictions and the number of true-negative molecule predictions determined based on a comparison between the set of molecule predictions and the set of training molecules.

Specific Example 14. The method of any of Specific Examples 1-13, wherein the first encoder, the second encoder, and the scoring model are not trained using decoy molecules.

Specific Example 15. The method of any of Specific Examples 1-14, wherein the embedding for the mass spectrometry spectrum is determined based on the mass spectrometry spectrum and supplemental experimental information, wherein the supplemental experimental information comprises at least one of: instrument type or fragmentation method.

Specific Example 16. A method for molecule identification, comprising: determining a first set of mass spectrometry spectra for a first set of molecules in a first sample; determining a second set of mass spectrometry spectra for a second set of molecules in a second sample; determining an embedding for each mass spectrometry spectrum in the first set of mass spectrometry spectra, using an encoder; determining an embedding for each mass spectrometry spectrum in the second set of mass spectrometry spectra, using the encoder; clustering the embeddings for each mass spectrometry spectrum in the first and second sets of mass spectrometry spectra into a set of clusters; identifying an embedding of interest based on the set of clusters; and identifying a molecule based on the embedding of interest, wherein the molecule is present in the second sample and is not present in the first sample.

Specific Example 17. The method of Specific Example 16, wherein the encoder encodes each mass spectrometry spectrum into an embedding space, wherein the embeddings are clustered within the embedding space.

Specific Example 18. The method of any of Specific Examples 16-17, wherein each cluster in the set of clusters has a cluster purity of at least 50%.

Specific Example 19. The method of any of Specific Examples 16-18, wherein identifying the molecule comprises: for each candidate molecule in a set of candidate molecules: determining an embedding for the candidate molecule based on a sequence for the candidate molecule, using a second encoder; and using a scoring model, determining a score for the candidate molecule based on the embedding of interest and the embedding for the candidate molecule; and selecting a candidate molecule from the set of candidate molecules based on the scores.

Specific Example 20. The method of any of Specific Examples 16-19, wherein the first sample and the second sample comprise samples from a multiple-arm experiment.

As used herein, "substantially" or other words of approximation (e.g., "about," "approximately," etc.) can be within a predetermined error threshold or tolerance of a metric, component, or other reference (e.g., within +/−0.001%, +/−0.01%, +/−0.1%, +/−1%, +/−2%, +/−5%, +/−10%, +/−15%, +/−20%, +/−30%, any range or value therein, of a reference).

All references cited herein are incorporated by reference in their entirety, except to the extent that the incorporated material is inconsistent with the express disclosure herein, in which case the language in this disclosure controls.

Different subsystems and/or modules discussed above can be operated and controlled by the same or different entities. In the latter variants, different subsystems can communicate via: APIs (e.g., using API requests and responses, API keys, etc.), requests, and/or other communication channels. Communications between systems can be encrypted (e.g., using symmetric or asymmetric keys), signed, and/or otherwise authenticated or authorized.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method for molecule identification, comprising:
    training a first encoder using a known match between a training sample and a set of training spectra, the training sample comprising a set of training molecules, wherein training the first encoder comprises:
        using the first encoder, determining a set of molecule predictions based on the set of training spectra, wherein a number of true-positive molecule predictions and a number of true-negative molecule predictions are determined based on a comparison between the set of molecule predictions and the set of training molecules;
        determining a loss for the set of molecule predictions, the loss comprising an accuracy metric determined based on the number of true-positive molecule predictions and the number of true-negative molecule predictions; and
        training the first encoder based on the loss;
    determining a mass spectrometry spectrum for a molecule;
    determining an embedding for the mass spectrometry spectrum, using the first encoder;
    for each candidate molecule in a set of candidate molecules:
        determining an embedding for the candidate molecule based on a sequence for the candidate molecule, using a second encoder; and
        using a scoring model, determining a score for the candidate molecule based on the embedding for the mass spectrometry spectrum and the embedding for the candidate molecule; and
    selecting a candidate molecule from the set of candidate molecules based on the scores.

2. The method of claim 1, wherein determining the score for the candidate molecule comprises: determining a similarity metric based on the embedding for the mass spectrometry spectrum and the embedding for the candidate molecule; and determining the score based on the similarity metric.

3. The method of claim 2, wherein the similarity metric comprises a distance between the embedding for the mass spectrometry spectrum and the embedding for the candidate molecule.

4. The method of claim 1, wherein the first encoder comprises a CNN.

5. The method of claim 4, wherein the first encoder further comprises a transformer.

6. The method of claim 1, wherein the second encoder comprises a combination of an RNN and a transformer.

7. The method of claim 1, wherein the mass spectrometry spectrum comprises an experimental dataset containing intensities across at least two dimensions, wherein a first dimension of the experimental dataset is mass to charge ratio (m/z) and a second dimension of the experimental dataset is retention time.

8. The method of claim 7, wherein the experimental dataset contains intensities across a third dimension, wherein the third dimension is ion mobility.

9. The method of claim 1, wherein the first encoder is configured to accommodate receiving as input experimental datasets with a variable number of dimensions.

10. The method of claim 1, further comprising determining a location of a post-translational modification within the candidate molecule based on the embedding for the mass spectrometry spectrum and the embedding for the candidate molecule.

11. The method of claim 1, wherein individual matches between each training spectrum in the set of training spectra and a corresponding training molecule in the set of training molecules is not known, wherein the set of molecule predictions is determined using the first encoder, the second encoder, and the scoring model.

12. The method of claim 11, wherein the loss for the set of molecule predictions is further determined based on a second set of molecule predictions determined using at least two first-generation search engines.

13. The method of claim 1, wherein the first encoder, the second encoder, and the scoring model are not trained using decoy molecules.

14. The method of claim 1, wherein the embedding for the mass spectrometry spectrum is determined based on the mass spectrometry spectrum and supplemental experimental information, wherein the supplemental experimental information comprises at least one of: instrument type or fragmentation method.

15. A method for molecule identification, comprising:
    training an encoder using a known match between a training sample and a set of training spectra, the training sample comprising a set of training molecules, wherein training the encoder comprises:
        using the encoder, determining a set of molecule predictions based on the set of training spectra, wherein a number of true-positive molecule predictions and a number of true-negative molecule predictions are determined based on a comparison between the set of molecule predictions and the set of training molecules;
        determining a loss for the set of molecule predictions, the loss comprising an accuracy metric determined based on the number of true-positive molecule predictions and the number of true-negative molecule predictions; and
        training the encoder based on the loss;
    determining a first set of mass spectrometry spectra for a first set of molecules in a first sample;
    determining a second set of mass spectrometry spectra for a second set of molecules in a second sample;
    determining an embedding for each mass spectrometry spectrum in the first set of mass spectrometry spectra, using the encoder;

determining an embedding for each mass spectrometry spectrum in the second set of mass spectrometry spectra, using the encoder;
clustering the embeddings for each mass spectrometry spectrum in the first and second sets of mass spectrometry spectra into a set of clusters;
identifying an embedding of interest based on the set of clusters; and
identifying a molecule based on the embedding of interest, wherein the molecule is present in the second sample and is not present in the first sample.

16. The method of claim 15, wherein the encoder encodes each mass spectrometry spectrum into an embedding space, wherein the embeddings are clustered within the embedding space.

17. The method of claim 15, wherein each cluster in the set of clusters has a cluster purity of at least 50%.

18. The method of claim 15, wherein identifying the molecule comprises:
for each candidate molecule in a set of candidate molecules:
determining an embedding for the candidate molecule based on a sequence for the candidate molecule, using a second encoder; and
using a scoring model, determining a score for the candidate molecule based on the embedding of interest and the embedding for the candidate molecule; and
selecting a candidate molecule from the set of candidate molecules based on the scores.

19. The method of claim 15, wherein the first sample and the second sample comprise samples from a multiple-arm experiment.

* * * * *